United States Patent
Takimoto et al.

(10) Patent No.: US 11,802,153 B2
(45) Date of Patent: Oct. 31, 2023

(54) ANTI-CD47 AGENT-BASED OVARIAN CANCER THERAPY

(71) Applicant: FORTY SEVEN, INC., Foster City, CA (US)

(72) Inventors: Chris Hidemi Mizufune Takimoto, Menlo Park, CA (US); Mark Ping Chao, Mountain View, CA (US); Jens-Peter Volkmer, Menlo Park, CA (US)

(73) Assignee: Forty Seven, Inc., Foster City, CA (US)

( * ) Notice: Subject to any disclaimer, the term of this patent is extended or adjusted under 35 U.S.C. 154(b) by 89 days.

(21) Appl. No.: 16/756,673

(22) PCT Filed: Oct. 18, 2018

(86) PCT No.: PCT/US2018/056441
§ 371 (c)(1),
(2) Date: Apr. 16, 2020

(87) PCT Pub. No.: WO2019/079548
PCT Pub. Date: Apr. 25, 2019

(65) Prior Publication Data
US 2020/0283520 A1  Sep. 10, 2020

Related U.S. Application Data

(60) Provisional application No. 62/573,835, filed on Oct. 18, 2017.

(51) Int. Cl.
| | | |
|---|---|---|
| C07K 16/28 | (2006.01) | |
| A61K 39/395 | (2006.01) | |
| A61P 35/00 | (2006.01) | |
| A61K 45/06 | (2006.01) | |
| A61K 39/00 | (2006.01) | |

(52) U.S. Cl.
CPC ...... *C07K 16/2803* (2013.01); *A61K 39/3955* (2013.01); *A61K 45/06* (2013.01); *A61P 35/00* (2018.01); *A61K 2039/505* (2013.01); *A61K 2039/54* (2013.01); *A61K 2039/545* (2013.01)

(58) Field of Classification Search
CPC combination set(s) only.
See application file for complete search history.

(56) References Cited

FOREIGN PATENT DOCUMENTS

| | | |
|---|---|---|
| CN | 105102479 A | 11/2015 |
| CN | 106999517 A | 8/2017 |
| CN | 107207593 A | 9/2017 |
| WO | WO-2009/091601 A1 | 7/2009 |
| WO | WO-2011/034969 A1 | 3/2011 |
| WO | WO-2011/041453 A1 | 4/2011 |
| WO | WO-2012/088309 A1 | 6/2012 |
| WO | WO-2013/109752 A1 | 7/2013 |
| WO | WO-2014/149477 A1 | 9/2014 |
| WO | WO-2014/179132 A1 | 11/2014 |
| WO | WO-2014/186761 A2 | 11/2014 |
| WO | WO-2015/138600 A2 | 9/2015 |
| WO | WO-2016/022994 A2 | 2/2016 |
| WO | WO-2016/023001 A1 | 2/2016 |
| WO | WO-2016/065329 A1 | 4/2016 |
| WO | WO-2016/118754 A1 | 7/2016 |
| WO | WO-2016/179399 A1 | 11/2016 |
| WO | WO-2016/191305 A1 | 12/2016 |
| WO | WO-2017/019767 A1 | 2/2017 |
| WO | WO-2017/035480 A1 | 3/2017 |
| WO | WO-2017049251 A2 * | 3/2017 ............... A61P 7/06 |
| WO | 2017/121771 A1 | 7/2017 |
| WO | 2017/127707 A1 | 7/2017 |
| WO | WO-2017117196 A1 | 7/2017 |
| WO | WO-2017/181033 A1 | 10/2017 |
| WO | WO-2018/026600 A1 | 2/2018 |
| WO | WO-2018/031419 A1 | 2/2018 |
| WO | WO-2018/081448 A1 | 5/2018 |
| WO | WO-2018/165015 A1 | 9/2018 |
| WO | 2017/100462 A2 | 12/2018 |
| WO | WO-2019/079548 A1 | 4/2019 |
| WO | WO-2019/079549 A1 | 4/2019 |
| WO | WO-2019/241403 A1 | 12/2019 |
| WO | WO-2020/068431 A1 | 4/2020 |
| WO | WO-2020/160285 A1 | 8/2020 |
| WO | WO-2020/163692 A1 | 8/2020 |

OTHER PUBLICATIONS

Fleury et al., "Structural Evidence for Recognition of a Single Epitope by Two Distinct Antibodies," Structure, Function, and Genetics 40, pp. 572-578 (2000) (Year: 2000).*

Ledermann et al., "Optimal treatment for relapsing ovarian cancer," Annals of Oncology 21 (Supplement 7) pp. vii218-vii222 (2010) (Year: 2010).*

Willingham et al., "The CD47-signal regulatory protein alpha (SIRPa) interaction is a therapeutic target for human solid tumors," PNAS (109)17, pp. 6662-6667 and supporting pp. 1-6 (Apr. 24, 2012) (Year: 2012).*

Domcke et al., "Evaluating cell lines as tumour models by comparison of genomic profiles," Nature Communications, 4:2126, pp. 1-10 (2013) (Year: 2013).*

Volkmer et al., "Overcoming immune evasion in ovarian and breast cancer with anti-CD47 antibody blockade: A novel class of immune therapy," European Journal of Cancer 50, Suppl. 5, p. S13 (2014). (Year: 2014).*

(Continued)

*Primary Examiner* — Bridget E Bunner
*Assistant Examiner* — Fozia M Hamud
(74) *Attorney, Agent, or Firm* — Choate, Hall & Stewart LLP; Rolando Medina; Melissa M. Adams

(57) ABSTRACT

Methods, kits, and compositions are provided herein that can be used to treat ovarian cancer using an anti-CD47 antibody. The anti-CD47 antibody can be used alone or in combination with one or more additional agent such as chemotherapy.

17 Claims, 8 Drawing Sheets
Specification includes a Sequence Listing.

(56) References Cited

OTHER PUBLICATIONS

National Clinical Trial NCT02216409: History of Changes for Study Phase I Trial of Hu5F9-G4, "A First-in-Human Phase 1 Dose Escalation Trial of Hu5F9-G4 in Patients With Advanced Solid Malignancies," pp. 1-6, Aug. 12, 2014 (earliest version on record) (Year: 2014).*

Liu et al., "Pre-Clinical Development of a Humanized Anti-CD47 Antibody with Anti-Cancer Therapeutic Potential," PLoS ONE 10(9) pp. 1-23 (2015) (Year: 2015).*

Kathawala et al., "The anti-CD47 antibody Hu5F9-G4 activates macrophages and inhibits ovarian cancer xenografts, alone and in combination with chemotherapy or immunotherapy," Proceedings: AACR 107th Annual Meeting, pp. 1-2, Apr. 16-20, 2016 (Year: 2016).*

Brightwell et al., "The CD47 'don't eat me signal' is highly expressed in human ovarian cancer," Gynecologic Oncology 143 pp. 393-397 (2016) (Year: 2016).*

Weiskopf et al., "CD47-blocking immunotherapies stimulate macrophage-mediated destruction of small-cell lung cancer," Clin Invest. 126(7) pp. 2610-2620 (2016) (Year: 2016).*

Evans et al., "PARP inhibitors in ovarian cancer: evidence, experience and clinical potential," Ther Adv Med Oncol, vol. 9(4) pp. 253-267 (2017) (Year: 2017).*

Liu et al., "CD47 promotes ovarian cancer progression by inhibiting macrophage phagocytosis," Oncotarget, vol. 8, (No. 24), pp. 39021-39032 (2017) (Year: 2017).*

Bourquard et al., "MAbTope: A Method for Improved Epitope Mapping," J Immunol, 201 (10) pp. 3096-3105 (Nov. 15, 2018) (Year: 2018).*

Raybould et al., "Public Baseline and shared response structures support the theory of antibody repertoire functional commonality," PNAS 116 (10) pp. 4025-4030 (Mar. 5, 2019) (Year: 2019).*

Lo et al., "Conformational epitope matching and prediction based on protein surface spiral features," BMC Genomics vol. 22, Article No. 116, pp. 1-16 (2021) (Year: 2021).*

Wong et al., "Ab-Ligity: identifying sequence-dissimilar antibodies that bind to the same epitope," mAbs, 13:1, pp. 1-9 (2021) (Year: 2021).*

Akbar et al., "A compact vocabulary of paratope-epitope interactions enables predictability of antibody-antigen binding," Cell Reports 34, 108856, pp. 1-5 and e1-e5, (Mar. 16, 2021 ) (Year: 2021).*

Hamanishi, et al., "Safety and antitumor activity of anti-PD-1 antibody, nivolumab, in patients with platinum-resistant ovarian cancer," Journal of Clinical Oncology, 33(34), pp. 4015-4022 (Year: 2015).*

Liu, X. et al., "CD47 blockade triggers T cell-mediated destruction of immunogenic tumors," Nature Medicine, 21(10), pp. 1209-1215 (Year: 2015).*

Jiang et al. "Targeting CD47 for cancer immunotherapy,"J Hematol Oncol. 14(1):180 pp. 1-18 (Year: 2021).*

PCT/US2018/056441—International Search Report and Wirtten Opinion dated Dec. 20, 2018, 17 pages.

PCT/US2018/056441—International Preliminary Report on Patentability dated Apr. 30, 2020, 9 pages.

Anonymous: "Trial of Hu5F9-G4 in Combination With Cetuximab in Patients With Solid Tumors and Advanced Colorectal Cancer", ClinicalTrials.gov, Nov. 3, 2016, pp. 1-8, XP055532527, Retrieved from the Internet: URL:https://clinicaltrials.gov/ct2/show/NCT02953782 [retrieved on Dec. 11, 2018].

Anonymous: "A Trial of Hu5F9-G4 With Avelumab in Ovarian Cancer", ClinicalTrials.gov, Jun. 15, 2018, pp. 1-6, XP55532523, Retrieved from the Internet: URL:https:// clinicaltrials.gov/ct2/show/NCT03558139 [retrieved on Dec. 11, 2018].

Oronsky, B. et al., A brief review of the management of platinum-resistant-platinum-refractory ovarian cancer, Med Oncol, 34(103):1-7 (2017).

Sikic, B. et al., First-in-Human, First-in-Class Phase I Trial of the Anti-CD47 Antibody Hu5F9-G4 in Patients With Advanced Cancers, J. Clin. Oncol., 37(12):946-953 (2019).

Anonymous, A Trial of Hu5F9-G4 with Avelumab in Ovarian Cancer, ClinicalTrials.gov, retrieved on Dec. 11, 2018 from https://clinicaltrials.gov/ct2/show/NC, pp. 1-6 (Jun. 15, 2018).

Chao, M.P. et al., The anti-CD47 antibody Hu5F9-G4 is a novel immune checkpoint inhibitor with synergistic efficacy in combination with clinically active cancer targeting antibodies, Cancer Immunol Res, 4(11 Supplement): Abstract PR13 (2016).

Diedrichs, S. Non-coding RNAs in Cancer, European Journal of Cancer, 50(Supp. 5): p. S13 (2014).

International Search Report for PCT/US2018/056442 (Treatment of Ovarian Cancer With ANTI-CD47 and ANTI-PD-L1, filed Oct. 18, 2018) received by ISA/EP, 4 pages (Jan. 18, 2019).

Kathawala, R. et al., Abstract 4001: The anti-CD47 antibody Hu5F9-G4 activates macrophages and inhibits ovarian cancer xenografts, alone and in combination with chemotherapy or immunotherapy, Cancer Research, 76(14): 3 pages (2016).

Sikic, B. et al., First-in-Human, First-in-Class Phase I Trial of the Anti-CD47 Antibody Hu5F9-G4 in Patients With Advanced Cancers, J Clin Oncol, 37:946-953 (2019).

Sockolosky, J. et al., Durable antitumor responses to CD47 blockade require adaptive immune stimulation, PNAS, 113(19):E2646-E2654 (2016).

Written Opinion for PCT/US2018/056442 (Treatment of Ovarian Cancer With Anti- CD47 and ANTI-PD-L1, filed Oct. 18, 2018) received by ISA/EP, 6 pages (Jan. 18, 2019).

Hu, W. et al., Research progress on the molecular mechanism of PD-L1 expression regulation in tumors, Chinese Journal of Immunology, 21:2634-2639 (2021).

Liu, Q. et al., New Advances in Diagnosis and Treatment of Gynecological Tumors, People's Military Medical Publishing House, 2(1):115-116 (2015).

Morse, C. B., et al., Elevated tumor mutational burden and prolonged clinical response to anti-PD-L1 antibody in platinum-resistant recurrent ovarian cancer, Gynecol. Oncol. Rep., 21:78-80 (2017).

Pfizer Clinical Protocol, pp. 1-126 (Dec. 15, 2016).

Yang, M. et al., Research progress on the relationship between CD47 and lymphoma, Journal of Cancer Control and Treatment, 6:33-36 (2014).

* cited by examiner

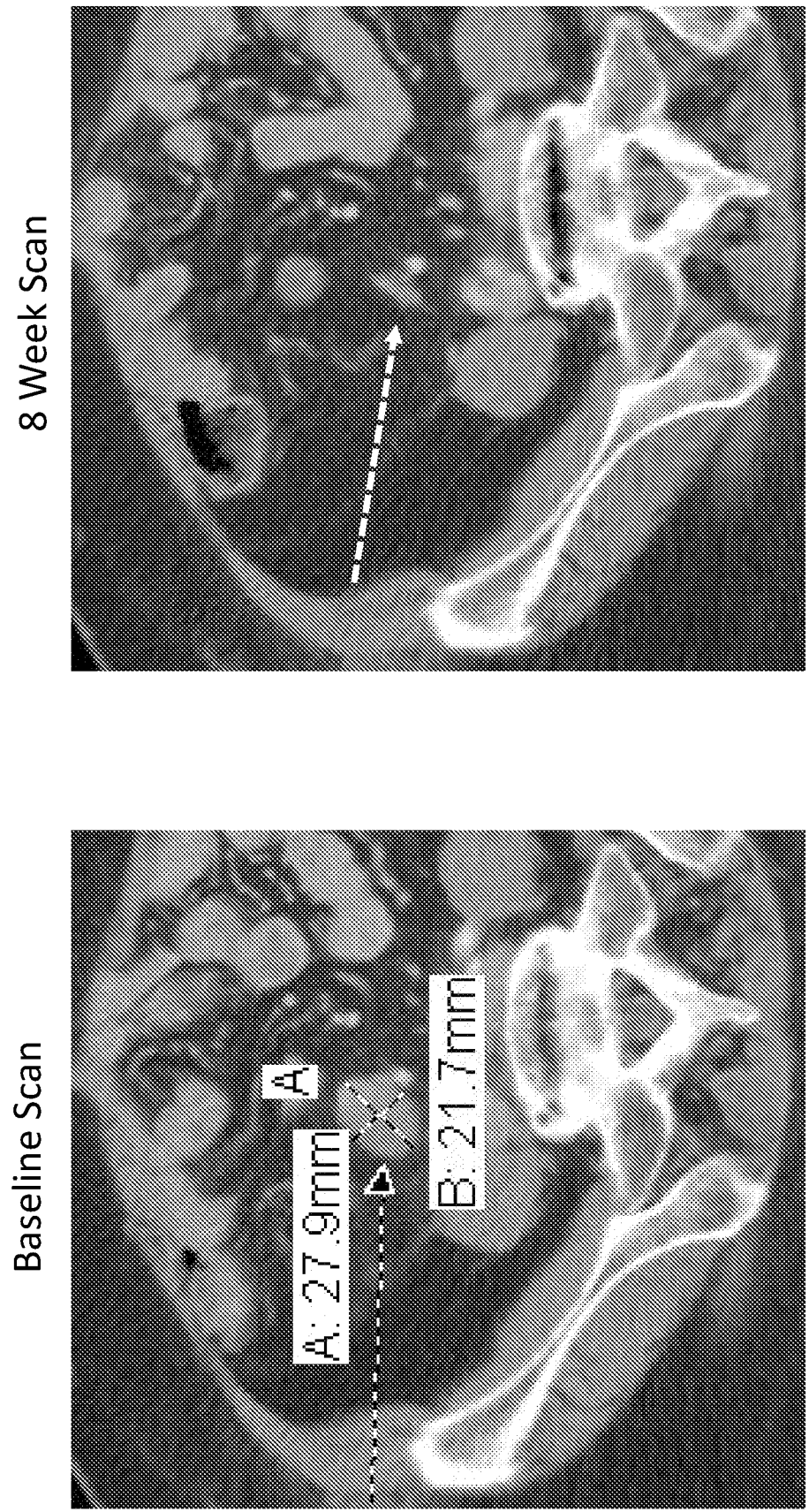
Figure 2: Pt 11-305 Restaging Scans

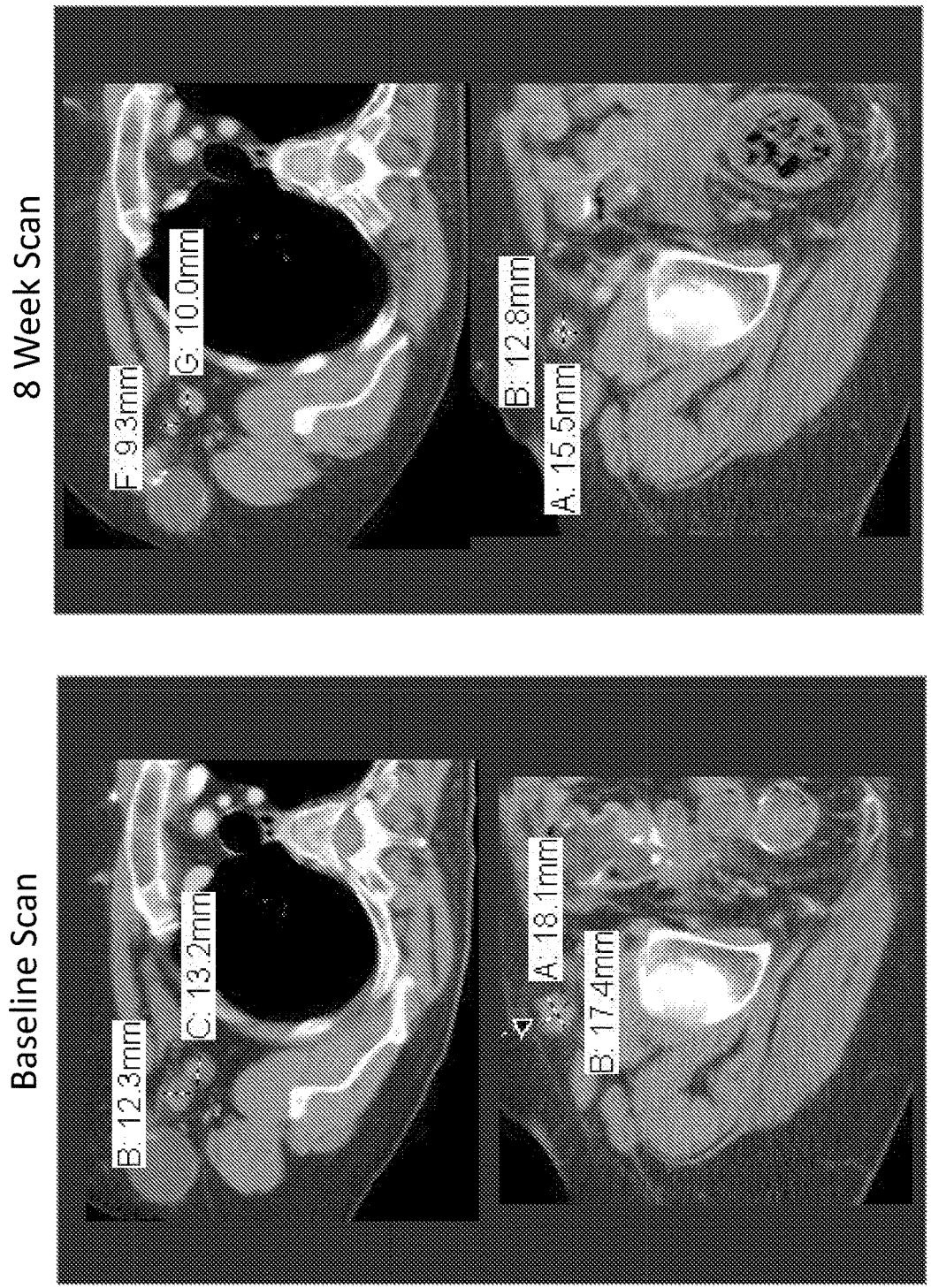
Figure 3: Pt 11-305 Restaging Scans

Figure 4: Pt 11-305 Restaging Scans
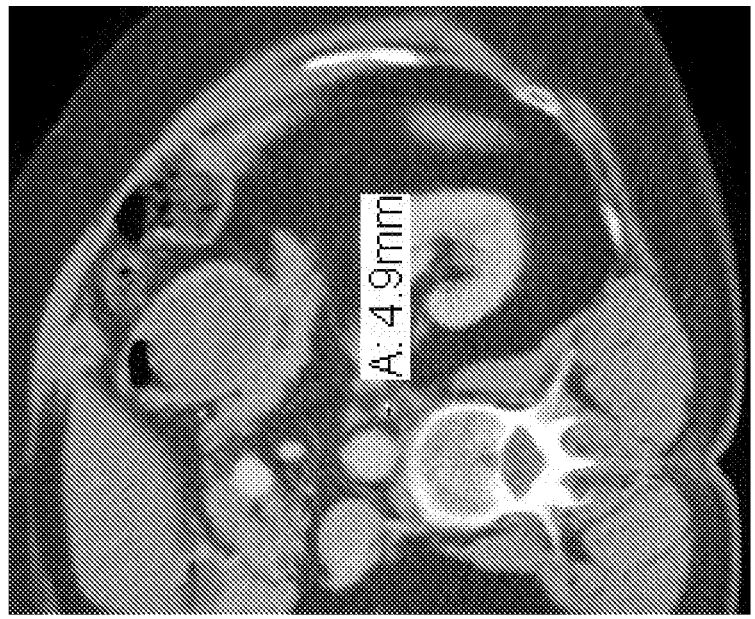
8 Week Scan
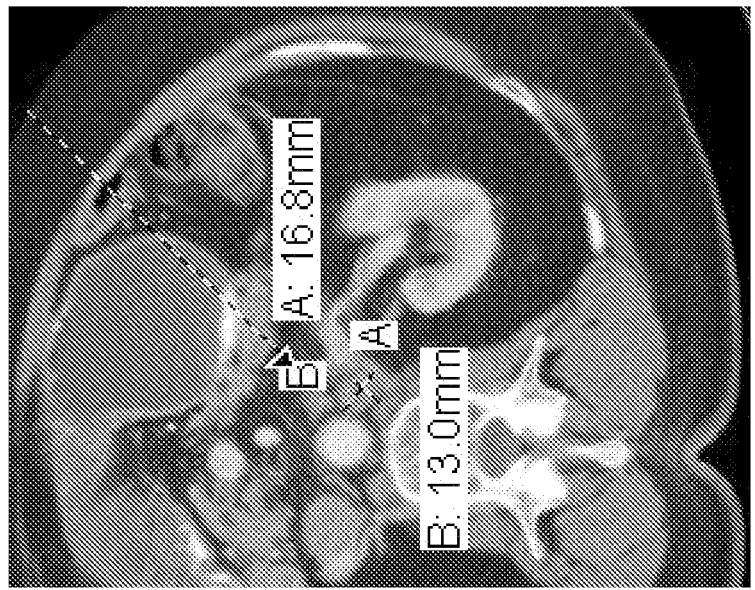
Baseline Scan

Figure 5: Pt 01-312 Restaging Scans: Left Para-Aortic Lymph Node
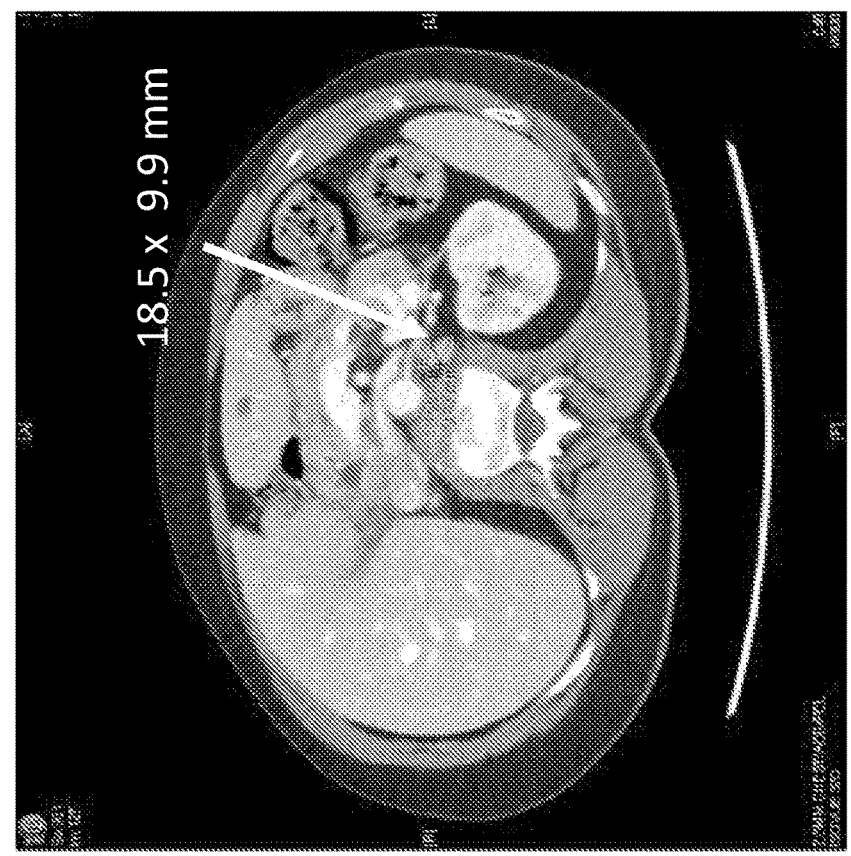
Baseline Scan
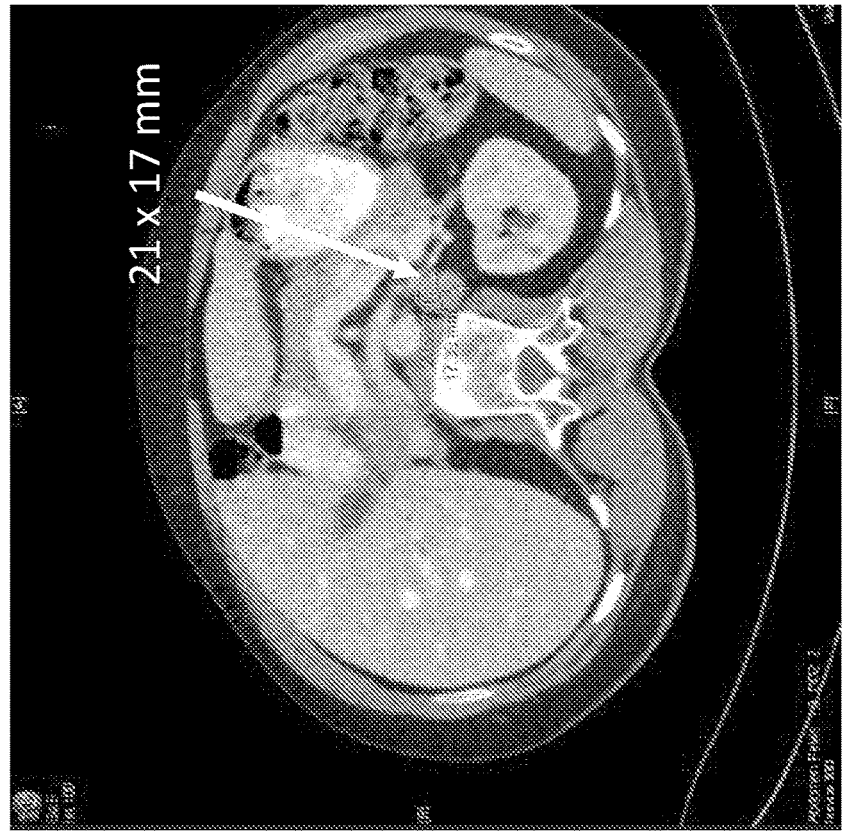
8 Week Scan

Figure 6: Pt 01-312 Restaging Scans: Porta Hepatis Lymph Node
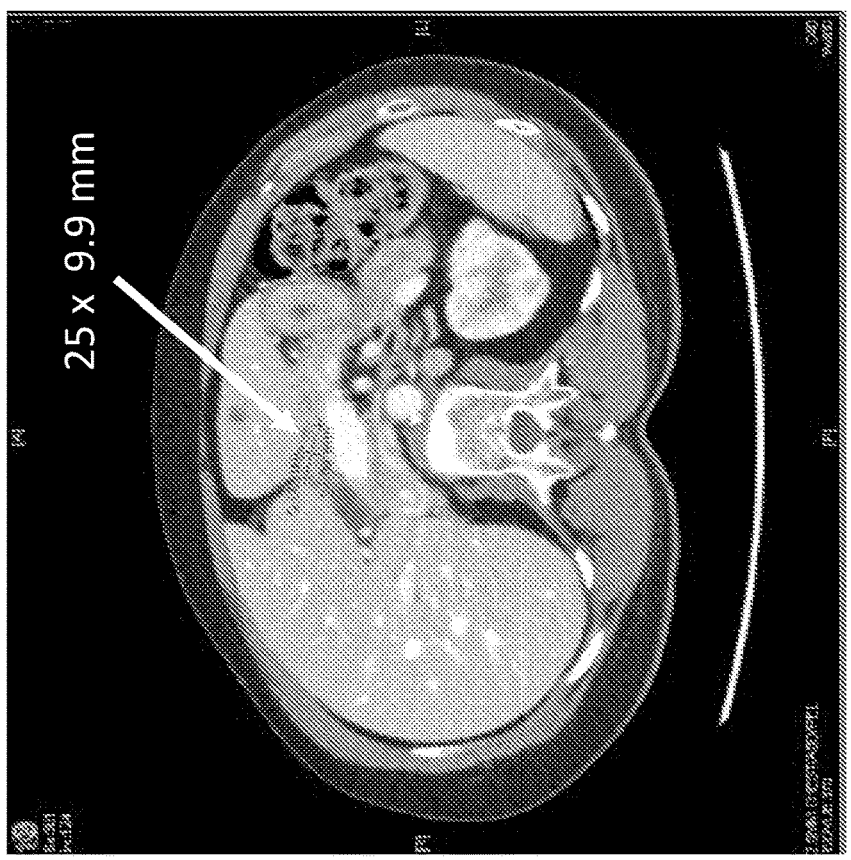
8 Week Scan
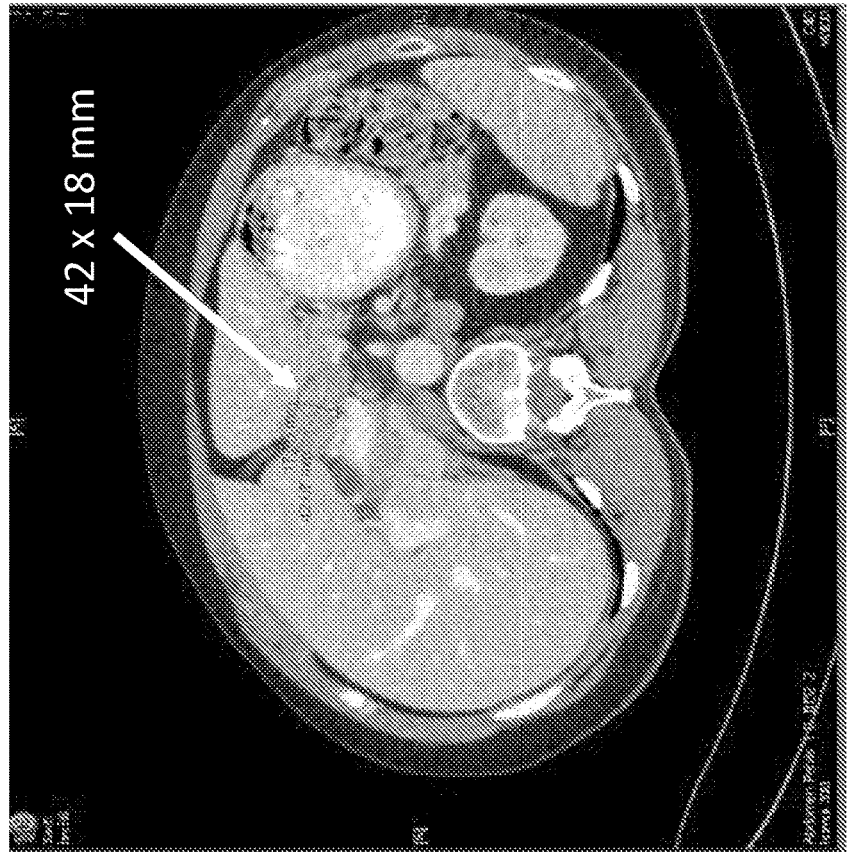
Baseline Scan Figure 7: Pt 01-312 Restaging Scans: Retrocaval Lymph Node
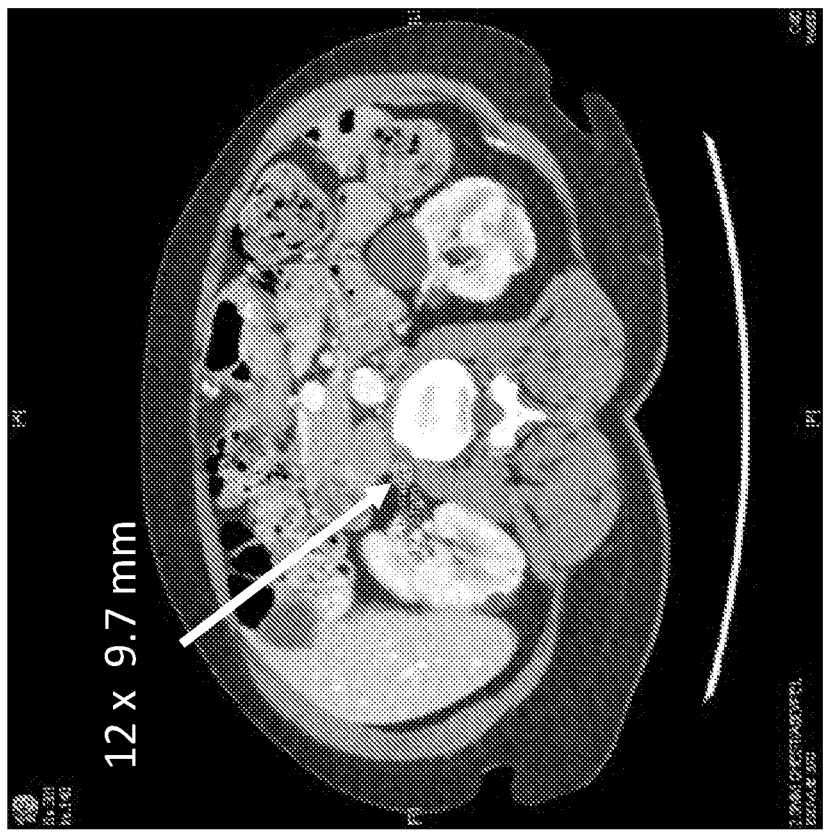
8 Week Scan
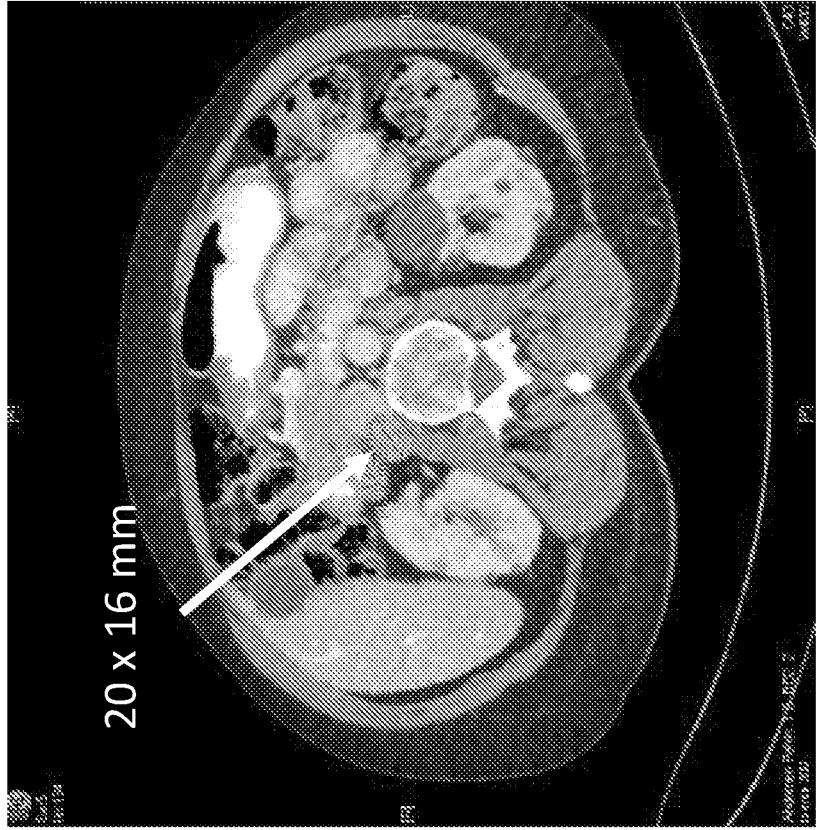
Baseline Scan

Figure 8: Pt 01-312 Restaging Scans: Periportal Lymph Node
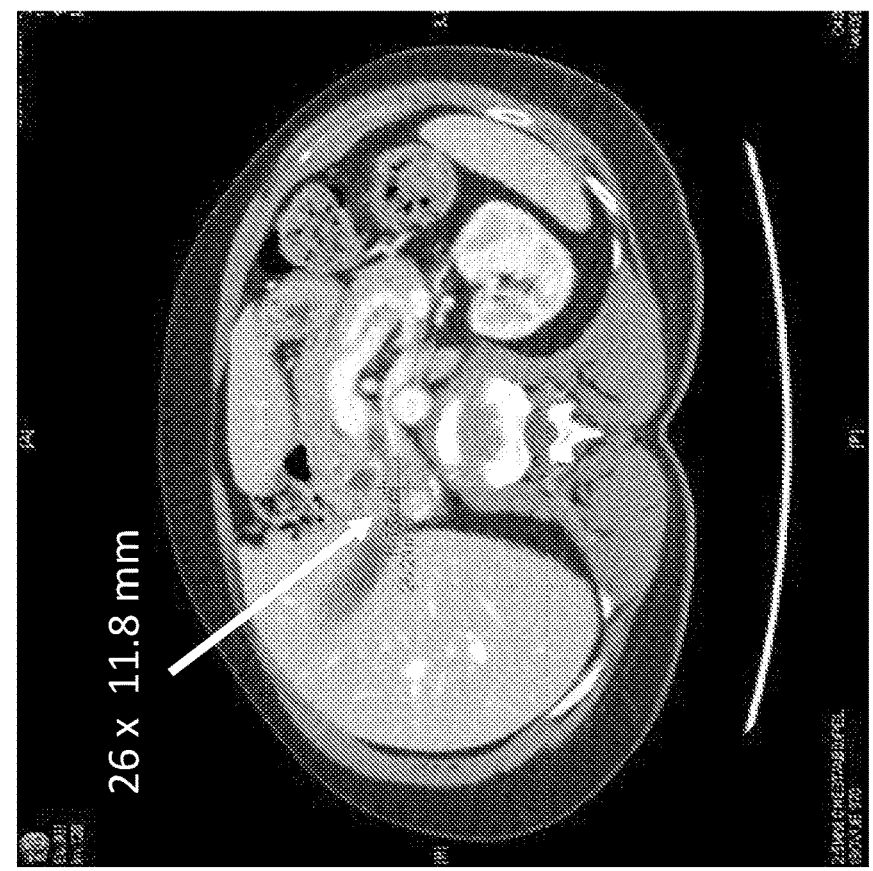
8 Week Scan
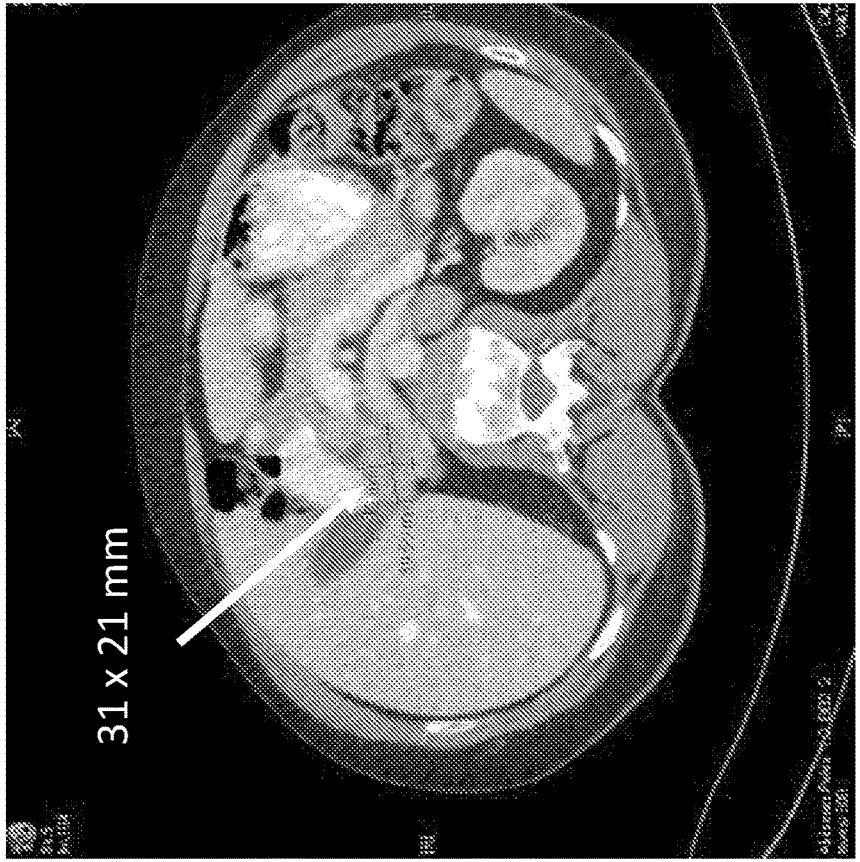
Baseline Scan

ANTI-CD47 AGENT-BASED OVARIAN CANCER THERAPY

CROSS REFERENCE TO RELATED APPLICATIONS

This application is the National Stage of International Application No. PCT/US2018/056441, filed Oct. 18, 2018, which claims benefit of U.S. Provisional Application No. 62/573,835, filed Oct. 18, 2017, which is hereby incorporated in its entirety by reference for all purposes.

SEQUENCE LISTING

The instant application contains a Sequence Listing which has been submitted electronically in ASCII format and is hereby incorporated by reference in its entirety. Said ASCII copy, created on Apr. 15, 2020, is named FSI002WOUS_SequenceListing.txt and is 6,241 bytes in size.

BACKGROUND

The large majority of cancers worldwide are solid tumors. In 2016, it is estimated that over 1,600,000 people will be newly diagnosed with a malignant solid tumor in the US (Siegel et al. (2016), Cancer statistics, 2016. CA: A Cancer Journal for Clinicians, 66:7-30). Current standards of care for solid tumors include surgical excision, radiotherapy, cytotoxic chemotherapy, and molecularly targeted small molecules and monoclonal antibodies (mAbs). Despite these therapies, most patients with metastatic cancer will die of the disease and/or treatment complications. Small molecules that target cancers have limited efficacy as single agents because of pre-existing or emergent resistance and usually exhibit toxicity to normal cells.

The development of therapeutic antibodies has substantially impacted treatment of some types of cancer. Conventionally these recombinant proteins specifically bind cancer cells and either block signaling pathways or mark them for destruction by the immune system. However, targeted antibodies exist for only a few cancers, even the most effective antibodies may require combination therapy with conventional chemotherapy, and often produce an incomplete therapeutic response. In many patients, the disease becomes resistant to antibodies treatment by loss of the antibody target (when the molecule is not essential for tumor cell survival) or by developing resistance to tumor killing. Usually patients experience a relapse of their disease.

CD47 has been identified as a key molecule mediating cancer cell evasion of phagocytosis by the innate immune system. CD47 appears to be an indispensable means by which cancer cells, including cancer stem cells, overcome intrinsic expression of their prophagocytic, "eat me," signals. The progression from normal cell to cancer cell involves changes in genes and/or gene expression that trigger programmed cell death (PCD) and programmed cell removal (PCR). Many of the steps in cancer progression subvert the multiple mechanisms of PCD, and the expression of the dominant antiphagocytic signal, CD47, may represent an important checkpoint.

CD47 expression is increased on the surface of cancer cells from a large number of diverse human tumor types including the following primary malignancies: head and neck, melanoma, breast, lung, ovarian, pancreatic, colon, bladder, prostate, leiomyosarcoma, glioblastoma, medulloblastoma, oligodendroglioma, glioma, lymphoma, leukemia, and multiple myeloma. In murine xenograft studies, it has been shown that CD47-blocking antibodies inhibit human cancer growth and metastasis by enabling the phagocytosis and elimination of cancer stem cells and cancer cells from various hematologic malignancies and several solid tumors.

CD47 serves as the ligand for SIRPα, which is expressed on phagocytic cells including macrophages and dendritic cells. When SIRPα is activated by CD47 binding, it initiates a signal transduction cascade resulting in inhibition of phagocytosis. In this way, CD47 functions as an antiphagocytic signal by delivering a dominant inhibitory signal to phagocytic cells. It has been demonstrated that a blocking anti-CD47 antibody enabled the phagocytic elimination of cancer stem cells and cancer cells.

In mouse xenografts, CD47-blocking antibodies inhibit human xenograft tumor growth and metastasis by enabling the phagocytosis and elimination of cancer cells from various hematologic malignancies and solid tumors. Furthermore, CD47 blocking antibodies synergize with the established cancer cell targeting antibodies rituximab, trastuzumab, and cetuximab to enhance therapeutic efficacy in some tumor types.

Methods for effective delivery of antibodies that block CD47 are of clinical interest, and are provided herein.

SUMMARY

Disclosed herein is a method of treating a human subject having an epithelial ovarian cancer or reducing the size of the epithelial ovarian cancer in the human subject, comprising administering an anti-CD47 agent to the subject. An anti-CD47 agent can include an anti-CD47 antibody.

The epithelial ovarian cancer can be serous tumor, mucinous tumor, clear cell tumor, endometriod tumor, transitional cell tumor, Brenner tumor, carcinosarcoma tumor, mixed epithelial tumor, borderline epithelial tumor, undifferentiated carcinoma tumor, fallopian tube tumor, or primary peritoneal tumor. In some aspects, the epithelial ovarian cancer is serous tumor. In some aspects, the serous ovarian cancer is low grade or high grade as determined by histological analysis subtyping.

In some aspects, the methods disclosed herein further comprise administering at least one additional agent to the human subject.

Also disclosed herein is a method of treating a human subject having ovarian cancer or reducing the size of the epithelial ovarian cancer in the human subject, comprising administering an anti-CD47 agent to the human subject; and administering at least one additional agent to the human subject. An anti-CD47 agent can include an anti-CD47 antibody.

The additional agent can comprise at least one of a chemotherapeutic agent, a VEGF inhibitor, a PARP inhibitor, an immune checkpoint inhibitor, an immuno-oncology agent, and a folate inhibitor.

In some aspects, the additional agent is a chemotherapeutic agent. In some aspects, the chemotherapeutic agent is Platinum (cisplatin/carboplatin). In some aspects, the chemotherapeutic agent is Taxane (paclitaxel (TAXOL®) or docetaxel (TAXOTERE®)), Gemcitabine, Albumin-bound paclitaxel (nab-paclitaxel, ABRAXANE®), Altretamine (HEXALEN®), Capecitabine (XELODA®), Cyclophosphamide (CYTOXAN®), Etoposide (VP-16), Gemcitabine (GEMZAR®), Ifosfamide (IFEX®), Irinotecan (CPT-11, CAMPTOSAR®), Liposomal doxorubicin (DOXIL®), Melphalan, Pemetrexed (ALIMTA®), Topotecan, Vinorelbine (NAVELBINE®), or Trabectedin (YONDELIS®).

In some aspects, the additional agent is a VEGF inhibitor, optionally bevacizumab (AVASTIN®), regorafenib (STIVARGA®), or aflibercept (EYLEA®).

In some aspects, the additional agent is a PARP inihibitor, optionally the PARP inhibitor is Rucaparib (RUBRACA®), Niraparib (ZEJULA®), Olaparib (LYNPARZA®), Talazoparib (BMN-673), or Veliparib (ABT-888).

In some aspects, the additional agent is an immune checkpoint inhibitor, optionally wherein the additional agent inhibits at least one of CTLA4, PD1, and PDL1.

In some aspects, the additional agent is a folate inhibitor that inhibits folate metabolism or targets the folate receptor.

In some aspects, the anti-CD47 antibody and the additional agent are administered concurrently or sequentially.

In some aspects, the anti-CD47 antibody comprises an IgG4 Fc. In some aspects, the anti-CD47 antibody competes for binding to CD47 with Hu5F9-G4. In some aspects, the anti-CD47 binds to the same CD47 epitope as Hu5F9-G4. In some aspects, the anti-CD47 antibody is Hu5F9-G4.

In some aspects, the antibody is formulated in a pharmaceutical composition with a pharmaceutically acceptable excipient.

In some aspects, the human subject is platinum sensitive.

In some aspects, the human subject is platinum resistant.

In some aspects, the anti-CD47 antibody is administered intravenously. In some aspects, the anti-CD47 antibody is administered intra-abdominally. In some aspects, the anti-CD47 antibody is administered intra-tumorally.

In some aspects, administration reduces the level of CA125 in the subject compared to baseline, optionally wherein the level of CA125 is measured about once per month. In some aspects, administration reduces the level of CA125 in the subject by at least 30-90, 40-80, 50-70, 30, 40, 50, 60, 70, 80, or 90% compared to baseline. CA125 can be measured with an immunoassay. CA125 can be measured using one or more of the assays disclosed in Mongia et al., *Performance characteristics of seven automated CA125 assays*. Am J Clin Pathol. 2006 June; 125(6):921-7; herein incorporated by reference for all purposes.

In some aspects, administration reduces the size of the cancer or metastases thereof compared to baseline, optionally as measured by imaging, optionally wherein the imaging is CT/PET/CT or Mill, optionally comprising disease that increases initially from baseline but subsequently decreases in size.

In some aspects, administration reduces the level of at least one of CA125, HE4 (human epididymis protein 4), CA-72-4, CA-19-9, and CEA; compared to baseline.

In some aspects, ovarian cancer is an epithelial ovarian cancer, optionally serous tumor, mucinous tumor, clear cell tumor, endometriod tumor, transitional cell tumor, Brenner tumor, carcinosarcoma tumor, mixed epithelial tumor, borderline epithelial tumor, undifferentiated carcinoma tumor, fallopian tube tumor, or primary peritoneal tumor. In some aspects, the ovarian cancer is a serous tumor. In some aspects, the serous tumor is low grade or high grade as determined by histological analysis.

In some aspects, tumor type is determined by histological analysis.

In some aspects, a method disclosed herein further comprises administering a priming dose of anti-CD47 antibody. In some aspects, a method disclosed herein further comprises administering a priming dose of an erythropoietin stimulating agent.

In some aspects, anti-CD47 antibody is administered to the subject as a priming dose ranging from about 0.5 to about 5 mg/kg of antibody, optionally 1 mg/kg of antibody. In some aspects, anti-CD47 antibody is administered to the subject as a dose ranging from about 20 to about 67.5 mg/kg of antibody, optionally 20 mg/kg of antibody, 30 mg/kg of antibody, 45 mg/kg of antibody, 60 mg/kg of antibody, or 67.5 mg/kg of antibody. In some aspects, anti-CD47 antibody is administered to the subject weekly, every 2 weeks, or every 3 weeks.

The method of any of the above claims, wherein the method comprises: (a) administering a priming dose of anti-CD47 antibody to the subject, wherein the priming dose is from about 0.5 to about 5 mg/kg of antibody; and (b) administering a therapeutically effective dose of anti-CD47 antibody to the subject, wherein step (b) is performed after at least about 3 to 14 days after beginning step (a), optionally being 7 days after (a).

In some aspects, the method comprises (a) administering the priming dose of anti-CD47 antibody to the subject at a dose of 1 mg/kg of antibody on day 1; and (b) administering the therapeutically effective dose of the anti-CD47 antibody to the subject at a dose of 20 mg/kg of antibody, 30 mg/kg of antibody, 45 mg/kg of antibody, 60 mg/kg of antibody, or 67.5 mg/kg of antibody on day 8.

In some aspects, effectiveness of the priming dose is determined based on the anemia status of the subject following administration of the priming dose. In some aspects, the priming dose is considered effective if: the fall in the subject's hemoglobulin level is not less than 8.0 g/dL; and/or the absolute fall in the subject's hemoglobin level is less than 3.0 to 3.75 g/dL.

In some aspects, a method disclosed herein further comprises after step (a) and prior to step (b): a step of determining whether administration of the priming dose was effective. In some aspects, the determining step comprises performing a reticulocyte count, wherein administration of the priming dose is determined to have been effective if the reticulocyte count is from about $100 \times 10^9$ reticulocytes per L to about $\sim 1000 \times 10^9$ reticulocytes per L. In some aspects, the determining step comprises performing a reticulocyte count, wherein administration of the priming dose is determined to have been effective if the percentage of reticulocytes in the blood is greater than about 1.5%. In some aspects, the determining step comprises performing a reticulocyte count, wherein administration of the primer agent is determined to have been effective if the reticulocyte index is greater than about 2%.

In some aspects, the priming dose is administered to the human subject in an infusate with a concentration of from about 0.05 mg/ml to about 0.5 mg/ml of anti-CD47 antibody.

The method of claim [0038], wherein the infusate is delivered over of a period of at least about 1-3, 8-10, 1, 2, 3, 4, 5, 6, 7, 8, 9, or 10 hour(s). In some aspects, the infusate is delivered over a period of at least about 3 hours. In some aspects, the infusate is delivered over a period of from about 2.5 hours to about 6 hours.

In some aspects, the priming dose is delivered by continuous pump over a period of from about 6 hours to about 3 days.

In some aspects, the priming dose is delivered subcutaneously.

In some aspects, the priming dose saturates at least about 50% to 100% of CD47 sites on red blood cells, optionally 100% of CD47 sites on red blood cells. In some aspects, the dose is determined by a receptor occupancy assay, in which following administration of a dose of unlabeled anti-CD47 agent to the subject, a blood sample is obtained and combined with a saturating dose of detectably labeled anti-CD47 antibody; and determining the level of binding.

In some aspects, the therapeutically effective dose of (b) is sufficient to achieve a circulating level of greater than 100, 250, 500, or 1000 µg/ml of the anti-CD47 antibody for a sustained period of time, optionally wherein the sustained period of time is at least 1-28, 7-28, 7-21, 14-28, or 21-28 days. In some aspects, the sustained period of time is from about 1, 2, 3, or 4 weeks.

In some aspects, the anti-CD47 antibody priming dose is 1 mg/kg of antibody.

In some aspects, the therapeutically effective anti-CD47 antibody dose is 20 mg/kg of antibody.

In some aspects, the therapeutically effective anti-CD47 antibody dose is 30 mg/kg of antibody.

In some aspects, the therapeutically effective anti-CD47 antibody dose is 45 mg/kg of antibody.

In some aspects, the therapeutically effective anti-CD47 antibody dose is 60 mg/kg of antibody.

In some aspects, the therapeutically effective anti-CD47 antibody dose is 67.5 mg/kg of antibody.

In some aspects, the therapeutically effective anti-CD47 antibody dose is administered from about every 7, 14, 21, or 28 days.

In some aspects, the therapeutically effective anti-CD47 antibody dose is administered every 7 days.

Also disclosed herein is a method of treating a human subject having a non-epithelial ovarian cancer, comprising administering an anti-CD47 agent to the subject, optionally wherein the non-epithelial ovarian cancer is a malignant-sex cord tumor or a malignant germ cell tumor. An anti-CD47 agent can include an anti-CD47 antibody.

Also disclosed herein is a composition comprising an anti-CD47 agent and at least one additional agent, optionally wherein the additional agent is a chemotherapeutic agent, a VEGF inhibitor, a PARP inhibitor, an immune checkpoint inhibitor, an immuno-oncology agent, or a folate inhibitor. An anti-CD47 agent can include an anti-CD47 antibody.

Also disclosed herein is a kit comprising an anti-CD47 agent, at least one additional agent, and instructions for use, optionally wherein the additional agent is a chemotherapeutic agent, a VEGF inhibitor, a PARP inhibitor, an immune checkpoint inhibitor, an immuno-oncology agent, or a folate inhibitor. An anti-CD47 agent can include an anti-CD47 antibody.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 2 shows scans of 11-305 at baseline and 8 weeks post-Hu-5F9-G4 administration. The change in tumor size is indicated in each.

FIG. 3 shows scans of 11-305 at baseline and 8 weeks post-Hu-5F9-G4 administration. The change in tumor size is indicated in each.

FIG. 4 shows scans of 11-305 at baseline and 8 weeks post-Hu-5F9-G4 administration. The change in tumor size is indicated in each.

FIG. 5 shows scans of 01-312 at baseline and 8 weeks post-Hu-5F9-G4 administration (left para-aortic lymph node). The change in tumor size is indicated in each.

FIG. 6 shows scans of 01-312 at baseline and 8 weeks post-Hu-5F9-G4 administration (porta hepatis lymph node). The change in tumor size is indicated in each.

FIG. 7 shows scans of 01-312 at baseline and 8 weeks post-Hu-5F9-G4 administration (retrocaval lymph node). The change in tumor size is indicated in each.

FIG. 8 shows scans of 01-312 at baseline and 8 weeks post-Hu-5F9-G4 administration (periportal lymph node). The change in tumor size is indicated in each.

DETAILED DESCRIPTION

Figure 1:
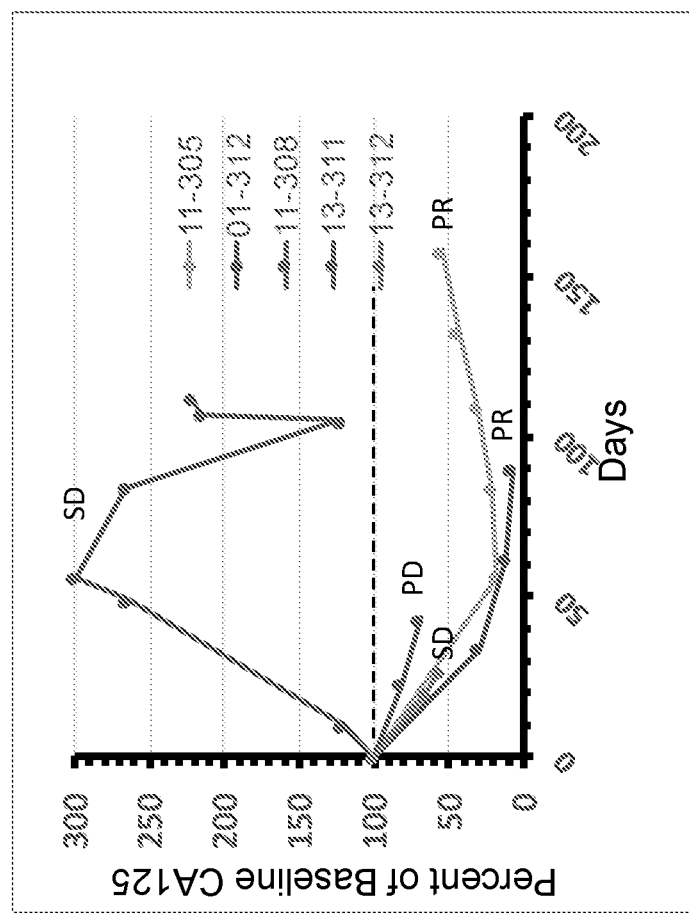
FIG. 1 shows the percent (%) change of CA125 relative to baseline in each of the five (5) ovarian cancer patients administered Hu-5F9-G4.

The present invention relates to methods of treating a subject with ovarian cancer with an anti-CD47 agent such as Hu5F9-G4.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limit of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, the term "anti-CD47 agent" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα. In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent (further described below). In an exemplary assay, target cells are incubated in the presence or absence of the candidate agent. An agent for use in the methods of the invention will up-regulate phagocytosis by at least 10% (e.g., at least 20%, at least 30%, at least 40%, at least 50%, at least 60%, at least 70%, at least 80%, at least 90%, at least 100%, at least 120%, at least 140%, at least 160%, at least 180%, or at least 200%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding.

When CD47 is activated, a process akin to apoptosis (i.e., programmed cell death) may occur (Manna and Frazier, Cancer Research, 64, 1026-1036, Feb. 1, 2004). Thus, in some embodiments, the anti-CD47 agent does not directly induce cell death of a CD47-expressing cell.

Some pathogens (e.g., pox viruses, Myxoma virus, Deerpox virus, swinepox virus, goatpox virus, sheeppox virus, etc.) express a CD47-analog (i.e., a CD47 mimic) (e.g., the M128L protein) that acts as a virulence factor to enable infection (Cameron et al., Virology. 2005 Jun. 20; 337(1): 55-67), and some pathogens induce the expression of endogenous CD47 in the host cell. Cells infected with a pathogen that expresses a CD47-analog may therefore express the pathogen-provided CD47 analog either exclusively or in combination with endogenous CD47. This mechanism allows the pathogen to increase CD47 expression (via expression of the CD47 analog) in the infected cell with or without increasing the level of endogenous CD47. In some embodiments, an anti-CD47 agent (e.g., anti-CD47 antibody, a SIRPα reagent, a SIRPα antibody, a soluble CD47 polypeptide, etc.) can reduce the binding of a CD47 analog (i.e., a CD47 mimic) to SIRPα. In some cases, a suitable anti-CD47 agent (e.g., a SIRPα reagent, an anti-CD47 antibody, etc.) can bind a CD47 analog (i.e., a CD47 mimic) to reduce the binding of the CD47 analog to SIRPα. In some cases, a suitable anti-CD47 agent (e.g., an anti-SIRPα antibody, a soluble CD47 polypeptide, etc.) can bind to SIRPα. A suitable anti-CD47 agent that binds SIRPα does not activate SIRPα (e.g., in the SIRPα-expressing phagocytic cell). An anti-CD47 agent can be used in any of the methods provided herein when the pathogen is a pathogen that provides a CD47 analog. In other words the term "CD47," as used herein, encompasses CD47 as well as CD47 analogs (i.e., CD47 mimics).

A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα. In some embodiments, a SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

In some embodiments, a subject anti-CD47 agent is a "high affinity SIRPα reagent", which includes SIRPα-derived polypeptides and analogs thereof. High affinity SIRPα reagents are described in international application PCT/US13/21937, which is hereby specifically incorporated by reference. High affinity SIRPα reagents are variants of the native SIRPα protein. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

A high affinity SIRPα reagent comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα with modified amino acid residues to increase affinity. In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules. The amino acid changes that provide for increased affinity are localized in the d1 domain, and thus high affinity SIRPα reagents comprise a dl domain of human SIRPα, with at least one amino acid change relative to the wild-type sequence within the dl domain. Such a high affinity SIRPα reagent optionally comprises additional amino acid sequences, for example antibody Fc sequences; portions of the wild-type human SIRPα protein other than the dl domain, including without limitation residues 150 to 374 of the native protein or fragments thereof, usually fragments contiguous with the dl domain; and the like. High affinity SIRPα reagents may be monomeric or multimeric, i.e. dimer, trimer, tetramer, etc.

In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between As used herein, an "anti-CD47 antibody" refers to any antibody that reduces the binding of CD47 (e.g., on a target cell) to SIRPα (e.g., on a phagocytic cell). Non-limiting examples are described in more detail below and include but are not limited to Hu5F9-G4. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')2, Fab, Fv and rIgG. The term also refers to recombinant single chain Fv fragments (scFv). The term antibody also includes bivalent or bispecific molecules, diabodies, triabodies, and tetrabodies. Additional description of the term antibody is found below.

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

As used herein, the phrase "platinum sensitive" refers to a human subject that develops recurrent disease greater than 6 months after receiving the last platinum-based chemotherapy.

As used herein, the phrase "platinum resistant" refers to a human subject that develops recurrent disease less than 6 months after receiving the last platinum-based chemotherapy.

As used herein, the term "baseline' is defined as a 30 day period prior to first treatment administration to human subject with ovarian cancer.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of the agents described herein. When administered in combination, each component can be administered at the same time or sequentially in any order at different points in time. Thus, each component can be administered separately but sufficiently closely in time so as to provide the desired therapeutic effect.

"Concomitant administration" of active agents in the methods of the invention means administration with the reagents at such time that the agents will have a therapeutic effect at the same time. Such concomitant administration may involve concurrent (i.e. at the same time), prior, or subsequent administration of the agents. A person of ordinary skill in the art would have no difficulty determining the appropriate timing, sequence and dosages of administration for particular drugs and compositions of the present invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

A "therapeutically effective amount" means the amount that, when administered to a subject for treating a disease, is sufficient to effect treatment for that disease.

Receptor occupancy (RO) assay measures the level of CD47 occupancy by CD47 binding agents, e.g., anti-CD47 antibody (Ab). The purpose of measuring the level of CD47 RO is to determine the relationship between the dose of a CD47 binding agent, the CD47 receptor saturation, and pharmacologic effect. The percent of receptor occupancy over time may provide useful information regarding the amount of drug or duration of exposure needed to produce the desired pharmacological effect. This assay can be used to determine the overall RO in the body by measuring the CD47 RO on surrogate cells, e.g. on CD45 negative (−) red blood cells (RBCs) and CD45 positive (+) white blood cells (WBCs), or other cell populations, e.g. bone marrow or tissue cells obtained through tissue biopsies. The RO assay can also be used to determine CD47 RO on target cells, e.g. RBC, leukemia cells or solid tumor cells, for CD47 binding and or blocking therapies.

Of interest is the use of this assay to determine the threshold of CD47 receptor occupancy that is correlated with the desired pharmacological effect. This threshold can be determined by assays performed ex vivo (in vitro) or by analysis of samples during in vivo dosing/treatment.

In one embodiment of the assay, a CD47 binding standard curve on a cell of interest cells is made by using fluorochrome-conjugated antibody at various concentrations. Receptor occupancy is measured by incubating the target cells with unlabeled antibody under different concentrations, and then the cells were either assayed in in vitro phagocytosis or incubated with a saturating concentration of labeled antibody based on the standard curve and analyzed for binding by flow cytometry. Receptor occupancy was calculated as follows:

$$\% \text{ RO}=100-((MFI_{test}-MFI_{unstained})(MFI_{saturated\ STD}-MFI_{unstained}))\times 100$$

In other embodiments the assay is performed by infusing a patient with a defined dose of antibody, obtaining a tissue sample, e.g. a blood sample, from the patient, usually before and after infusion of the antibody. The tissue sample is incubated with a saturating concentration of labeled antibody, and analyzed by flow cytometry. The analysis may be gated, for example, on red blood cells, white blood cells, cancer cells, etc.

It has been found that a priming dose that achieves at least about 80% saturation of CD47 on RBC is sufficient to induce compensation for anemia and reduce degree of anemia on subsequent doses. In humans, the priming dose has been found to be as discussed above, i.e. from about 0.5 mg/kg to about 5 mg/kg. In some embodiments of the invention, a receptor occupancy assay is performed with a candidate CD47 bind agent to determine the level of priming dose that provides for at least about 50% saturation on RBC, at least about 60% saturation, at least about 70% saturation, at least about 80% saturation, at least about 90% saturation, at least about 95% saturation, at least about 99% saturation, or more.

In some embodiments of the invention, a receptor occupancy assay is performed to determine the appropriate priming dose for a candidate anti-CD47 agent, e.g. an antibody that binds to CD47, a SIRPα polypeptide, etc.

Methods of Treatment

Methods are provided for treating a subject with a therapeutic dose of anti-CD47 agent. The subject methods include a step of administering a primer agent to subject, followed by a step of administering a therapeutically effective dose of an anti-CD47 agent to the subject. In some embodiments, the step of administering a therapeutically effective dose is performed after at least about 3 days (e.g., at least about 4 days, at least about 5 days, at least about 6 days, at least about 7 days, at least about 8 days, at least about 9 days, or at least about 10 days) after beginning the administration of a primer agent. This period of time is, for example, sufficient to provide for enhanced reticulocyte production by the individual.

The administration of a therapeutically effective dose of an anti-CD47 agent can be achieved in a number of different ways. In some cases, two or more therapeutically effective doses are administered after a primer agent is administered. Suitable administration of a therapeutically effective dose can entail administration of a single dose, or can entail administration of doses daily, semi-weekly, weekly, once every two weeks, once a month, annually, etc. In some cases, a therapeutically effective dose is administered as two or more doses of escalating concentration (i.e., increasing doses), where (i) all of the doses are therapeutic doses, or where (ii) a sub-therapeutic dose (or two or more sub-therapeutic doses) is initially given and therapeutic doses are achieved by said escalation. As one non-limiting example to illustrate escalating concentration (i.e., increasing doses), a therapeutically effective dose can be administered weekly, beginning with a sub-therapeutic dose (e.g., a dose of 5 mg/kg), and each subsequent dose can be increased by a particular increment (e.g., by 5 mg/kg), or by variable increments, until a therapeutic dose (e.g., 30 mg/kg) is reached, at which point administration may cease or may continue (e.g., continued therapeutic doses, e.g., doses of 30 mg/kg). As another non-limiting example to illustrate escalating concentration (i.e., increasing doses), a therapeutically effective dose can be administered weekly, beginning with a therapeutic dose (e.g., a dose of 10 mg/kg), and each subsequent dose can be increased by a particular increment (e.g., by 10 mg/kg), or by variable increments, until a therapeutic dose (e.g., 30 mg/kg, 100 mg/kg, etc.) is reached, at which point administration may cease or may continue (e.g., continued therapeutic doses, e.g., doses of 30 mg/kg, 100 mg/kg, etc.). In some embodiments, administration of a therapeutically effective dose can be a continuous infusion and the dose can altered (e.g., escalated) over time.

Dosage and frequency may vary depending on the half-life of the anti-CD47 agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. i.m., i.p., i.v., s.c., and the like.

An initial dose of a CD47 binding agent, including but not limited to a priming dose, may lead to hemagglutination for a period of time immediately following infusion. Without being bound by the theory, it is believed that the initial dose of a multivalent CD47 binding agent may cause cross-linking of RBC bound to the agent. In certain embodiments of the invention, a CD47 binding agent is infused to a patient in an initial dose, and optionally in subsequent doses, over a period of time and/or concentration that reduces the possibility of hematologic microenvironments where there is a high local concentration of RBC and the agent.

In some embodiments, an initial dose of a CD47 binding agent is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example from about 3 hours to about 4 hours. In some such embodiments, the dose of agent in the infusate is from about 0.05 mg/ml to about 0.5 mg/ml; for example from about 0.1 mg/ml to about 0.25 mg/ml.

In other embodiments, an initial dose of a CD47 binding agent, e.g. a priming dose, is administered by continuous fusion, e.g. as an osmotic pump, delivery patch, etc., where the dose is administered over a period of at least about 6 hours, at least about 12 hours, at least about 24 hours, at least about 2 days, at least about 3 days. Many such systems are known in the art. For example DUROS technology, provides a bi-compartment system separated by a piston. One of the compartments consists of osmotic engine specifically formulated with an excess of solid NaCl, such that it remains present throughout the delivery period and results in a constant osmotic gradient. It also consists of a semi permeable membrane on one end through which water is drawn into the osmotic engine and establishes a large and constant osmotic gradient between the tissue water and the osmotic engine. Other compartment consists of a drug solution with an orifice from which the drug is released due to the osmotic gradient. This helps to provide site specific and systemic drug delivery when implanted in humans. The preferred site of implantation is subcutaneous placement in the inside of the upper arm.

Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered, e.g. in a weekly dosing schedule. In some embodiments a therapeutically effective dose of an anti-CD47 agent is administered as two or more doses of escalating concentration, in others the doses are equivalent. There is reduced hemagglutination after the priming dose, and therefore the extended infusion time is not required.

Methods are provided for treating a human subject having ovarian cancer or reducing the size of the ovarian cancer, the method comprising administering to the subject an anti-CD47 antibody and an additional agent. Such methods include administering to a subject in need of treatment a therapeutically effective amount or an effective dose of the combined agents of the invention, including without limitation combinations with an ESA.

Additional agents can enhance the efficacy of anti-CD47 agents. The anti-CD47 antibody can be administered in combination or prior to the additional agent.

The additional agent can comprise at least one of a chemotherapeutic agent, a VEGF inhibitor, a PARP inhibitor, an immune checkpoint inhibitor, an immuno-oncology agent, and a folate inhibitor.

An anti-CD47 agent (e.g., Hu5F9-G4) can be administered with a chemotherapeutic agent.

An anti-CD47 agent (e.g., Hu5F9-G4) can be administered with a VEGF inhibitor.

An anti-CD47 agent (e.g., Hu5F9-G4) can be administered with a PARP inhibitor.

An anti-CD47 antibody (e.g., Hu5F9-G4) can be administered with an immune checkpoint inhibitor.

An anti-CD47 agent (e.g., Hu5F9-G4) can be administered with an immuno-oncology agent.

An anti-CD47 agent (e.g., Hu5F9-G4) can be administered with a folate inhibitor.

In some aspects, the additional agent is a chemotherapeutic agent. In some aspects, the chemotherapeutic agent is Platinum (cisplatin/carboplatin). In some aspects, the chemotherapeutic agent is Taxane (paclitaxel (TAXOL®) or docetaxel (TAXOTERE®)), Gemcitabine, Albumin-bound paclitaxel (nab-paclitaxel, ABRAXANE®), Altretamine (HEXALEN®), Capecitabine (XELODA®), Cyclophosphamide (CYTOXAN®), Etoposide (VP-16), Gemcitabine (GEMZAR®), Ifosfamide (IFEX®), Irinotecan (CPT-11, CAMPTOSAR®), Liposomal doxorubicin (DOXIL®), Melphalan, Pemetrexed (ALIMTA®), Topotecan, Vinorelbine (NAVELBINE®), or Trabectedin (YONDELIS®).

An anti-CD47 agent (e.g., Hu5F9-G4) can be administered with Platinum (e.g., cisplatin/carboplatin).

An anti-CD47 agent (e.g., Hu5F9-G4) can be administered with Taxane (e.g., paclitaxel (TAXOL®) or docetaxel (TAXOTERE®)).

An anti-CD47 agent (e.g., Hu5F9-G4) can be administered with Gemcitabine.

An anti-CD47 agent (e.g., Hu5F9-G4) can be administered with Albumin-bound paclitaxel (e.g., nab-paclitaxel, ABRAXANE®).

An anti-CD47 agent (e.g., Hu5F9-G4) can be administered with Altretamine (e.g., HEXALEN®).

An anti-CD47 agent (e.g., Hu5F9-G4) can be administered with Capecitabine (e.g., XELODA®).

An anti-CD47 agent (e.g., Hu5F9-G4) can be administered with Cyclophosphamide (e.g., CYTOXAN®).

An anti-CD47 agent (e.g., Hu5F9-G4) can be administered with Etoposide (e.g., VP-16).

An anti-CD47 agent (e.g., Hu5F9-G4) can be administered with Gemcitabine (e.g., GEMXAR®).

An anti-CD47 agent (e.g., Hu5F9-G4) can be administered with Ifosfamide (e.g., IFEX®).

An anti-CD47 agent (e.g., Hu5F9-G4) can be administered with Irinotecan (e.g., CPT-11, CAMPTOSAR®).

An anti-CD47 agent (e.g., Hu5F9-G4) can be administered with Liposomal doxorubicin (e.g., DOXIL®).

An anti-CD47 agent (e.g., Hu5F9-G4) can be administered with Melphalan.

An anti-CD47 agent (e.g., Hu5F9-G4) can be administered with Pemetrexed (e.g., ALIMTA®).

An anti-CD47 agent (e.g., Hu5F9-G4) can be administered with Topotecan.

An anti-CD47 agent (e.g., Hu5F9-G4) can be administered with Vinorelbine (e.g., NAVELBINE®).

An anti-CD47 agent (e.g., Hu5F9-G4) can be administered with Trabectedin (e.g., YONDELIS®).

In some aspects, the additional agent is a VEGF inhibitor, optionally bevacizumab (AVASTIN®), regorafenib (STIVARGA®), or aflibercept (EYLEA®).

An anti-CD47 agent (e.g., Hu5F9-G4) can be administered with bevacizumab (e.g., AVASTIN®).

An anti-CD47 agent (e.g., Hu5F9-G4) can be administered with regorafenib (e.g.,) STIVARGA®).

An anti-CD47 agent (e.g., Hu5F9-G4) can be administered with aflibercept (e.g., EYLEA®).

In some aspects, the additional agent is a PARP inihibitor, optionally the PARP inhibitor is Rucaparib (RUBRACA®), Niraparib (ZEJULA®), Olaparib (LYNPARZA®), Talazoparib (BMN-673), or Veliparib (ABT-888).

An anti-CD47 agent (e.g., Hu5F9-G4) can be administered with Rucaparib (e.g.,) RUBRACA®).

An anti-CD47 agent (e.g., Hu5F9-G4) can be administered with Niraparib (e.g., ZEJULA®).

An anti-CD47 agent (e.g., Hu5F9-G4) can be administered with Olaparib (e.g., LYNPARZA®).

An anti-CD47 agent (e.g., Hu5F9-G4) can be administered with Talazoparib (e.g., BMN-673).

An anti-CD47 agent (e.g., Hu5F9-G4) can be administered with Veliparib (e.g., ABT-888).

In some aspects, the additional agent is an immune checkpoint inhibitor, optionally wherein the additional agent inhibits at least one of CTLA4, PD1, and PDL1.

An anti-CD47 agent (e.g., Hu5F9-G4) can be administered with a CTLA4 inhibitor.

An anti-CD47 agent (e.g., Hu5F9-G4) can be administered with a PD1 inhibitor.

An anti-CD47 agent (e.g., Hu5F9-G4) can be administered with a PDL1 inhibitor.

In some aspects, the additional agent is a folate inhibitor that inhibits folate metabolism or targets the folate receptor.

An anti-CD47 agent (e.g., Hu5F9-G4) can be administered with a folate inhibitor that inhibits folate metabolism.

An anti-CD47 agent (e.g., Hu5F9-G4) can be administered with a folate inhibitor that targets the folate receptor.

A combination of an anti-CD47 antibody with an additional agent described herein is given to patients with tumors subtypes that are responsive to these therapies. These tumors may be defined by a higher frequency of mutations, resulting in more tumor antigens, therefore being more immunogenic, as described herein. In some embodiments patients treated with combination therapy are responsive to treatment with an immune activator or checkpoint inhibitor; however this represents a subset of approximately 25% of patients within a specific potentially responsive tumor subtype. In some embodiments, the individuals may be platinum therapy sensitive or resistant.

In some embodiments, the subject methods include a step of administering a primer agent to subject, followed by a step of administering a therapeutically effective dose of an anti-CD47 antibody and an additional agent to the subject. In some embodiments, the step of administering a therapeutically effective dose is performed after at least about 3 days (e.g., at least about 4 days, at least about 5 days, at least about 6 days, at least about 7 days, at least about 8 days, at least about 9 days, or at least about 10 days) after beginning the administration of a primer agent. This period of time is, for example, sufficient to provide for enhanced reticulocyte production by the individual.

The administration of a therapeutically effective dose of an anti-CD47 antibody and/or an additional agent can be achieved in a number of different ways. In some cases, two or more therapeutically effective doses are administered after a primer agent is administered. Suitable administration of a therapeutically effective dose can entail administration of a single dose, or can entail administration of doses daily, semi-weekly, weekly, once every two weeks, once a month, annually, etc. In some cases, a therapeutically effective dose is administered as two or more doses of escalating concentration (i.e., increasing doses), where (i) all of the doses are therapeutic doses, or where (ii) a sub-therapeutic dose (or two or more sub-therapeutic doses) is initially given and therapeutic doses are achieved by said escalation. As one non-limiting example to illustrate escalating concentration (i.e., increasing doses), a therapeutically effective dose can be administered weekly, beginning with a sub-therapeutic dose (e.g., a dose of 5 mg/kg), and each subsequent dose can be increased by a particular increment (e.g., by 5 mg/kg), or by variable increments, until a therapeutic dose (e.g., 30 mg/kg) is reached, at which point administration may cease or may continue (e.g., continued therapeutic doses, e.g., doses of 30 mg/kg). As another non-limiting example to illustrate escalating concentration (i.e., increasing doses), a therapeutically effective dose can be administered weekly, beginning with a therapeutic dose (e.g., a dose of 10 mg/kg), and each subsequent dose can be increased by a particular increment (e.g., by 10 mg/kg), or by variable increments, until a therapeutic dose (e.g., 30 mg/kg, 100 mg/kg, etc.) is reached, at which point administration may cease or may continue (e.g., continued therapeutic doses, e.g., doses of 30 mg/kg, 100 mg/kg, etc.). In some embodiments, administration of a therapeutically effective dose can be a continuous infusion and the dose can altered (e.g., escalated) over time.

Dosage and frequency may vary depending on the half-life of the anti-CD47 antibody and/or the additional agent in the patient. It will be understood by one of skill in the art that such guidelines will be adjusted for the molecular weight of the active agent, e.g. in the use of antibody fragments, in the use of antibody conjugates, in the use of SIRPα reagents, in the use of soluble CD47 peptides etc. The dosage may also be varied for localized administration, e.g. intranasal, inhalation, etc., or for systemic administration, e.g. i.m., i.p., i.v., s.c., and the like.

In certain embodiments of the invention, the anti-CD47 antibody is infused to a patient in an initial dose, and optionally in subsequent doses, over a period of time and/or concentration that reduces the possibility of hematologic microenvironments where there is a high local concentration of RBC and the agent.

In some embodiments of the invention, an initial dose of the anti-CD47 antibody is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example from about 3 hours to about 4 hours. In some such embodiments, the dose of agent in the infusate is from about 0.05 mg/ml to about 0.5 mg/ml; for example from about 0.1 mg/ml to about 0.25 mg/ml.

Ovarian Cancer

Provided herein are methods for treating individuals having an ovarian cancer or reducing the size of the ovarian cancer in the subject, comprising administering: a therapeutically effective amount of an anti-CD47 antibody to the subject; and, optionally a therapeutically effective amount of at least one additional agent to the subject.

Examples of ovarian cancer include epithelial ovarian cancer, optionally serous tumor, mucinous tumor, clear cell tumor, endometriod tumor, transitional cell tumor, Brenner tumor, carcinosarcoma tumor, mixed epithelial tumor, borderline epithelial tumor, undifferentiated carcinoma tumor, fallopian tube tumor, or primary peritoneal tumor.

In some embodiments, the epithelial ovarian cancer is serous tumor. The serous tumor ovarian cancer can be determined to be low grade or high grade by histological analysis subtyping. In one embodiment, the individuals are platinum chemotherapy sensitive. In another embodiment, the individuals are platinum chemotherapy resistant.

In some embodiments, the patient has a low mutation burden. In some embodiments, the patent has a high mutation burden. As is known in the art, cancer types can vary in the average or specific degree of mutation, where higher levels of mutation are associated with increased expression of neoantigens. See, for example, Vogelstein et al., (2013), supra. A low mutation burden can be a cancer type with an average per tumor, or specific number for an individual tumor, of up to about 10, up to about 20, up to about 30, up to about 40, up to about 50 non-synonymous mutations per tumor. A high mutation burden can be a cancer type with greater than about 50, greater than about 75, greater than about 100, greater than about 125, greater than about 150 non-synonymous mutations per tumor.

In some such embodiments the cancer is, without limitation, ovarian cancer. In some such embodiments, the cancer is a type that has a high neoantigen, or mutagenesis, burden (see Vogelstein et al. (2013) Science 339(6127):1546-1558, herein specifically incorporated by reference). In other embodiments, the cancer with a type with a low neoantigen burden. In some such embodiments, the combination therapy of the present invention enhances the activity of the checkpoint inhibitor. In other embodiments, where the individual cancer does not respond to a checkpoint inhibitor alone, the combination therapy provides a therapeutic response. In some embodiments, the individual is platinum sensitive. In other embodiments, the individual is platinum resistant.

Cancer

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, pre-malignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

Clinical Endpoints

The methods described herein result in at least one improved endpoint compared to baseline.

In some embodiments of the invention, administration of the anti-CD47 agent, with or without an additional agent, reduce the level of cancer markers such as CA125, HE4 (human epididymis protein 4), CA-72-4, CA-19-9, and CEA; compared to baseline. In some embodiments, administration of the anti-CD47 agent, with or without an additional agent, reduce CA125 in the subject compared to baseline. In some embodiments, the level of CA125 is measured about once per month. In other embodiments, administration reduces the level of CA125 in the subject by at least 30-90, 40-80, 50-70, 30, 40, 50, 60, 70, 80, or 90% compared to baseline. In other embodiments, administration reduces the size of the cancer or metastases thereof compared to baseline, optionally as measured by imaging, optionally wherein the imaging is CT/PET/CT or MRI, optionally comprising disease that increases initially from baseline but subsequently decreases in size.

As used herein, endpoints for treatment will be given a meaning as known in the art and as used by the Food and Drug Administration.

Overall survival is defined as the time from randomization until death from any cause, and is measured in the intent-to-treat population. Survival is considered the most reliable cancer endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased overall survival of patients.

Endpoints that are based on tumor assessments include DFS, ORR, TTP, PFS, and time-to-treatment failure (TTF). The collection and analysis of data on these time-dependent endpoints are based on indirect assessments, calculations, and estimates (e.g., tumor measurements). Disease-Free Survival (DFS) is defined as the time from randomization until recurrence of tumor or death from any cause. The most frequent use of this endpoint is in the adjuvant setting after definitive surgery or radiotherapy. DFS also can be an important endpoint when a large percentage of patients achieve complete responses with chemotherapy.

Objective Response Rate. ORR is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study.

Time to Progression and Progression-Free Survival. TTP and PFS have served as primary endpoints for drug approval. TTP is defined as the time from randomization until objective tumor progression; TTP does not include deaths. PFS is defined as the time from randomization until objective tumor progression or death. The precise definition of tumor progression is important and should be carefully detailed in the protocol.

Antibodies

The methods described herein include administration of an antibody or antibodies, i.e., administration of an anti CD47 antibody and, in some embodiments, administration of an additional antibody. As described above, the term "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies. The term "antibody" also includes antigen binding forms of antibodies, including fragments with antigen-binding capability (e.g., Fab', F(ab')$_2$, Fab, Fv and rIgG. The term also refers to recombinant single chain Fv fragments (scFv). The term antibody also includes bivalent or bispecific molecules, diabodies, triabodies, and tetrabodies.

Selection of antibodies may be based on a variety of criteria, including selectivity, affinity, cytotoxicity, etc. The phrase "specifically (or selectively) binds" to an antibody or "specifically (or selectively) immunoreactive with," when referring to a protein or peptide, refers to a binding reaction that is determinative of the presence of the protein, in a heterogeneous population of proteins and other biologics. Thus, under designated immunoassay conditions, the specified antibodies bind to a particular protein sequences at least two times the background and more typically more than 10 to 100 times background. In general, antibodies of the present invention bind antigens on the surface of target cells in the presence of effector cells (such as natural killer cells or macrophages). Fc receptors on effector cells recognize bound antibodies.

An antibody immunologically reactive with a particular antigen can be generated by recombinant methods such as selection of libraries of recombinant antibodies in phage or similar vectors, or by immunizing an animal with the antigen or with DNA encoding the antigen. Methods of preparing polyclonal antibodies are known to the skilled artisan. The antibodies may, alternatively, be monoclonal antibodies. Monoclonal antibodies may be prepared using hybridoma methods. In a hybridoma method, an appropriate host animal is typically immunized with an immunizing agent to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell.

Human antibodies can be produced using various techniques known in the art, including phage display libraries. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire.

Antibodies also exist as a number of well-characterized fragments produced by digestion with various peptidases. Thus pepsin digests an antibody below the disulfide linkages in the hinge region to produce F(ab)'$_2$, a dimer of Fab which itself is a light chain joined to V$_H$-C$_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin.

Antibodies of interest may be tested for their ability to induce ADCC (antibody-dependent cellular cytotoxicity) or ADCP (antibody dependent cellular phagocytosis). Antibody-associated ADCC activity can be monitored and quantified through detection of either the release of label or lactate dehydrogenase from the lysed cells, or detection of reduced target cell viability (e.g. Annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.).

Anti-CD47 Antibodies

The methods described herein include administration of an anti-CD47 antibody.

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2008) Mol Cell. 31(2):266-77; Hatherley et al. (2007) J.B.C. 282:14567-75; and the role of SIRPα cis dimerization in CD47 binding is discussed by Lee et al. (2010) J.B.C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

The term "anti-CD47 agent" or "agent that provides for CD47 blockade" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

In some embodiments, the subject anti-CD47 antibody specifically binds CD47 and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα and such an antibody can be referred to as a "non-blocking anti-CD47 antibody." A suitable anti-CD47 antibody that is an "anti-CD47 agent" can be referred to as a "CD47-blocking antibody". Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

In some embodiments an anti-CD47 antibody comprises a human IgG Fc region, e.g. an IgG1, IgG2a, IgG2b, IgG3, IgG4 constant region. In one embodiment the IgG Fc region is an IgG4 constant region. The IgG4 hinge may be stabilized by the amino acid substitution S241P (see Angal et al. (1993) Mol. Immunol. 30(1):105-108, herein specifically incorporated by reference).

In some embodiments, the anti-CD47 antibody competes for binding to CD47 with Hu5F9-G4. In some embodiments, the anti-CD47 binds to the same CD47 epitope as Hu5F9-G4.

In some embodiments, the methods described herein include administration of the anti-CD47 antibody Hu5F9-G4. In some embodiments, the methods described herein include administration of an anti-CD47 antibody with sequences (light chain, heavy chain and/or CDR) at least 97%, at least 98%, at least 99% or 100% identical to the sequences of Hu5f9-G4. Table 1 contains the sequence of the Hu5f9-G4 antibody heavy and light chains. The CDR regions are shown in bold.

TABLE 1

| SEQ ID NO | Description and Sequence |
|---|---|
| 1 | Hu5f9-G4 Antibody Heavy Chain<br>QVQLVQSGAEVKKPGASVKVSCKASGYTFTNYNMHWVRQA<br>PGQRLEWMGTIYPGNDDTSYNQKFKDRVTITADTSASTAY<br>MELSSLRSEDTAVYYCARGGYRAMDYWGQGTLVTVSSAST<br>KGPSVFPLAPCSRSTSESTAALGCLVKDYFPEPVTVSWNS<br>GALTSGVHTFPAVLQSSGLYSLSSVVTVPSSSLGTKTYTC<br>NVDHKPSNTKVDKRVESKYGPPCPPCPAPEFLGGPSVFLF<br>PPKPKDTLMISRTPEVTCVVVDVSQEDPEVQFNWYVDGVE<br>VHNAKTKPREEQFNSTYRVVSVLTVLHQDWLNGKEYKCKV<br>SNKGLPSSIEKTISKAKGQPREPQVYTLPPSQEEMTKNQV<br>SLTCLVKGFYPSDIAVEWESNGQPENNYKTTPPVLDSDGS<br>FFLYSRLTVDKSRWQEGNVFSCSVMHEALHNHYTQKSLSL<br>SLGK |
| 2 | Hu5f9-G4 Antibody Light chain<br>DIVMTQSPLSLPVTPGEPASISCRSSQSIVYSNGNTYLGW<br>YLQKPGQSPQLLIYKVSNRFSGVPDRFSGSGSGTDFTLKI<br>SRVEAEDVGVYYCFQGSHVPYTFGQGTKLEIKRTVAAPSV<br>FIFPPSDEQLKSGTASVVCLLNNFYPREAKVQWKVDNALQ<br>SGNSQESVTEQDSKDSTYSLSSTLTLSKADYEKHKVYACE<br>VTHQGLSSPVTKSFNRGEC |

Dosing

The methods described herein include administration of a therapeutically effective dose of compositions, i.e., a therapeutically effective dose of an anti-CD47 antibody and, optionally, an additional agent.

Compositions are administered to a patient in an amount sufficient to substantially ablate targeted cells, as described above. An amount adequate to accomplish this is defined as a "therapeutically effective dose", which may provide for an improvement in overall survival rates. Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

Effective doses of the combined agents of the present invention for the treatment of cancer vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

A therapeutically effective dose of the anti-CD47 antibody can depend on the specific agent used, but is usually about 20 mg/kg body weight or more (e.g., about 20 mg/kg or more, about 25 mg/kg or more, about 30 mg/kg or more, about 35 mg/kg or more, about 40 mg/kg or more, about 45 mg/kg or more, about 50 mg/kg or more, or about 55 mg/kg or more, or about 60 mg/kg or more, or about 65 mg/kg or more, or about 70 mg/kg or more), or from about 20 mg/kg to about 70 mg/kg (e.g., from about 20 mg/kg to about 67.5 mg/kg, or from about 20 mg/kg to about 60 mg/kg).

In some embodiments, the therapeutically effective dose of the anti-CD47 antibody is 20, 30, 45, 60, or 67.5 mg/kg. In some embodiments, the therapeutically effective dose of the anti-CD47 antibody is 20 to 60 mg/kg. In some embodiments, the therapeutically effective dose of the anti-CD47 antibody is 20 to 67.5 mg/kg.

The dose required to achieve and/or maintain a particular serum level of the administered composition is proportional to the amount of time between doses and inversely proportional to the number of doses administered. Thus, as the frequency of dosing increases, the required dose decreases. The optimization of dosing strategies will be readily understood and practiced by one of ordinary skill in the art. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

A "maintenance dose" is a dose intended to be a therapeutically effective dose. For example, in experiments to determine the therapeutically effective dose, multiple different maintenance doses may be administered to different subjects. As such, some of the maintenance doses may be therapeutically effective doses and others may be sub-therapeutic doses.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including carcinomas, hematologic cancers, melanomas, sarcomas, gliomas, etc. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Toxicity of the combined agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Primer Agents and Priming Dose

In some embodiments of the methods described herein, a primer agent is administered prior to administering a therapeutically effective dose of an anti-CD47 antibody to the individual. Suitable primer agents include an erythropoiesis-stimulating agent (ESA), and/or a priming dose of an anti-CD47 antibody. Following administration of the priming agent, and allowing a period of time effective for an increase in reticulocyte production, a therapeutic dose of an anti-CD47 antibody is administered. Administration may be made in accordance with the methods described in co-pending patent application U.S. Ser. No. 14/769,069, herein specifically incorporated by reference.

In some embodiments, administration of a combination of agents of the invention is combined with an effective dose of an agent that increases patient hematocrit, for example erythropoietin stimulating agents (ESA). Such agents are known and used in the art, including, for example, Aranesp→ (darbepoetin alfa), Epogen→$_{NF}$/Procrit→$_{NF}$(epoetin alfa), Omontys→(peginesatide), Procrit→, etc.

The term "priming dose" or as used herein refers to a dose of an anti-CD47 agent that primes a subject for administration of a therapeutically effective dose of anti-CD47 agent such that the therapeutically effective dose does not result in a severe loss of RBCs (reduced hematocrit or reduced hemoglobin). The specific appropriate priming dose of an anti-CD47 agent can vary depending on the nature of the agent used and on numerous subject-specific factors (e.g., age, weight, etc.). Examples of suitable priming doses of an anti-CD47 agent include from about 0.5 mg/kg to about 5 mg/kg, from about 0.5 mg/kg to about 4 mg/kg, from about 0.5 mg/kg to about 3 mg/kg, from about 1 mg/kg to about 5 mg/kg, from about 1 mg/kg to about 4 mg/kg, from about 1 mg/kg to about 3 mg/kg, about 1 mg/kg, about 2 mg/kg, about 3 mg/kg, about 4 mg/kg, about 5 mg/kg. In some embodiments, the priming does is preferably 1 mg/kg.

In some embodiments of the methods described herein, the anti-CD47 antibody is administered to the subject as a priming dose ranging from about 0.5 to about 5 mg/kg of antibody, optionally 1 mg/kg of antibody. In some embodiments, the anti-CD47 antibody is administered to the subject as a dose ranging from about 20 to about 67.5 mg/kg of antibody, optionally 20 mg/kg of antibody, 30 mg/kg of antibody, 45 mg/kg of antibody, 60 mg/kg of antibody, or 67.5 mg/kg of antibody.

In some embodiments of the invention, a primer agent is administered prior to administering a therapeutically effective dose of an anti-CD47 agent to the individual. Suitable primer agents include an erythropoiesis-stimulating agent (ESA), and/or a priming dose of an anti-CD47 agent. Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered. In some embodiments a therapeutically effective dose of an anti-CD47 agent is administered as two or more doses of escalating concentration, in others the doses are equivalent.

In some embodiments of the invention, an effective priming dose of Hu-5F9G4 is provided, where the effective priming dose for a human is around about 1 mg/kg, e.g. from at least about 0.5 mg/kg up to not more than about 5 mg/kg; from at least about 0.75 mg/kg up to not more than about 1.25 mg/kg; from at least about 0.95 mg/kg up to not more than about 1.05 mg/kg; and may be around about 1 mg/kg In some embodiments of the invention, an initial dose of a CD47 binding agent is infused over a period of at least about 2 hours, at least about 2.5 hours, at least about 3 hours, at least about 3.5 hours, at least about 4 hours, at least about 4.5 hours, at least about 5 hours, at least about 6 hours or more. In some embodiments an initial dose is infused over a period of time from about 2.5 hours to about 6 hours; for example from about 3 hours to about 4 hours. In some such embodiments, the dose of agent in the infusate is from about 0.05 mg/ml to about 0.5 mg/ml; for example from about 0.1 mg/ml to about 0.25 mg/ml.

In some embodiments a priming dose may be delivered through a subcutaneous route, by injection, patch, osmotic pump, and the like as known in the art.

Following administration of the priming agent, and allowing a period of time effective for an increase in reticulocyte production, a therapeutic dose of an anti-CD47 agent is administered. The therapeutic dose can be administered in number of different ways. In some embodiments, two or more therapeutically effective doses are administered after a primer agent is administered, e.g. in a weekly dosing schedule. In some embodiments a therapeutically effective dose of an anti-CD47 agent is administered as two or more doses of escalating concentration, in others the doses are equivalent.

In other embodiments, an initial dose of a CD47 binding agent, e.g. a priming dose, is administered by continuous fusion, e.g. as an osmotic pump, delivery patch, etc., where the dose is administered over a period of at least about 6 hours, at least about 12 hours, at least about 24 hours, at least about 2 days, at least about 3 days. Many such systems are known in the art. For example DUROS technology, provides a bi-compartment system separated by a piston. One of the compartments consists of osmotic engine specifically formulated with an excess of solid NaCl, such that it remains present throughout the delivery period and results in a constant osmotic gradient. It also consists of a semi permeable membrane on one end through which water is drawn into the osmotic engine and establishes a large and constant osmotic gradient between the tissue water and the osmotic engine. Other compartment consists of a drug solution with an orifice from which the drug is released due to the osmotic gradient. This helps to provide site specific and systemic drug delivery when implanted in humans. The preferred site of implantation is subcutaneous placement in the inside of the upper arm.

Following administration of the priming agent, and allowing a period of time effective for an increase in reticulocyte production, a therapeutic dose of the anti-CD47 antibody is administered. The therapeutic dose can be administered in number of different ways. In some embodiments, two or more therapeutically effective doses are administered after a primer agent is administered, e.g. in a weekly dosing schedule. In some embodiments a therapeutically effective dose of the anti-CD47 antibody is administered as two or more doses of escalating concentration, in others the doses are equivalent. There is reduced hemagglutination after the priming dose, and therefore the extended infusion time is not required.

Administration

In the methods described herein, compositions, e.g., an anti-CD47 antibody and, optionally, an additional agent, are administered to a subject. The compositions can be administered by parenteral, topical, intravenous, intra-abdominal, intratumoral, oral, subcutaneous, intraarterial, intracranial, intraperitoneal, intranasal or intramuscular means. A typical route of administration is intravenous or intratumoral, although other routes can be equally effective.

In some embodiments the anti-CD47 antibody and/or the additional agent is administered intra-abdominally. In some embodiments the anti-CD47 antibody and/or the additional agent is administered intravenously. In some embodiments the anti-CD47 antibody and/or the additional agent is administered intra-tumorally. In one embodiment, a priming dose of the anti-CD47 antibody is administered, and the priming dose is delivered subcutaneously. In some embodiments, the anti-CD47 antibody and the additional agent are administered concurrently. In some embodiments, the anti-CD47 antibody and the additional agent are administered sequentially.

The active agents are administered within a period of time to produce an additive or synergistic effect on depletion of cancer cells in the host. Methods of administration include, without limitation, systemic administration, intra-tumoral administration, etc. Usually the anti-CD47 antibody is administered within about a period of about 45 days, about 30 days, about 21 days, about 14 days, about 10 days, about 8 days, about 7 days, about 6 days, about 5 days, about 4 days, about 3 days, about 2 days, about 1 day or substantially the same day as the additional agent. In some embodiments the anti-CD47 antibody is administered prior to the additional agent. In some embodiments the anti-CD47 antibody is administered after the additional agent. The agents can be considered to be combined if administration scheduling is such that the serum level of both agents is at a therapeutic level at the same time. Administration may be repeated as necessary for depletion of the cancer cell population.

Pharmaceutical Compositions

The methods described herein include administration of pharmaceutical compositions comprising the anti-CD47 antibody and/or the additional agent.

Typically, the compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

Kits

Also described herein are kits comprising the active agents, e.g., an anti-CD47 antibody and, optionally, an additional agent, and formulations thereof, and instructions for use. The kit can further contain a least one additional reagent, e.g. a chemotherapeutic drug, ESA, etc. Kits typically include a label indicating the intended use of the contents of the kit. The term label includes any writing, or recorded material supplied on or with the kit, or which otherwise accompanies the kit.

Also provided are kits for use in the various methods disclosed herein. The subject kits include a primer agent and an anti-CD47 agent. In some embodiments, a kit comprises two or more primer agents. In some embodiments, a kit comprises two or more anti-CD47 agents. In some embodiments, a primer agent is provided in a dosage form (e.g., a priming dosage form). In some embodiments, a primer agent is provided in two or more different dosage forms (e.g., two or more different priming dosage forms). In some embodiments, an anti-CD47 agent is provided in a dosage form (e.g., a therapeutically effective dosage form). In some embodiments, an anti-CD47 agent is provided in two or more different dosage forms (e.g., two or more different therapeutically effective dosage forms). In the context of a kit, a primer agent and/or an anti-CD47 agent can be provided in liquid or sold form in any convenient packaging (e.g., stick pack, dose pack, etc.).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

Sequences

In some embodiments, the methods described herein include administration of antibodies with sequences described herein; e.g., the heavy chain, light chain, and/or CDR sequences described herein. The sequences of the administered antibodies can be, e.g., at least 95, 96, 97, 98, 99, or 100% identical to the sequences described herein.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (<www.ncbi.nlm.nih.gov/>)

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B(1992).

Example 1: Determination of Priming Dose for Anti-CD47 Antibody

In a Phase I clinical trial, human cancer patients were administered varying priming doses of Hu-5F9-G4 at 0.1 mg/kg (n=1), 0.3 mg/kg (n=2), 1.0 mg/kg (n=6), and 3.0 mg/kg (n=2).

Two dose limiting toxicities (DLTs) were observed (Grade 3 abdominal pain; hemagglutination) in the 3.0 mg/kg group. DLTs were not observed at 1.0 mg/kg. 1.0 mg/kg was selected as the priming dose for future study in human subjects.

Example 2: Ovarian Cancer Treatment with Anti-CD47 Antibody

Five female cancer patients with ovarian cancer were treated with Hu-5F9-G4 as a monotherapy. The dosing protocol and response of each as of July 2017 are summarized in Table A.

TABLE A

| Pt # | Patient | Dose | CA125 Nadir | Best Response | Rx Duration, Status |
|---|---|---|---|---|---|
| 11-305 | 71 yo Clear Cell Ov Ca | 20 mpk loading | 338 to 61 (−80%) | PR (−50%), confirmed | 22 wks, offstudy for PD |
| 01-312 | 68 yo Fallopian Tube Ca | 20 mpk weekly | 890 to 70 (−92%) | PR (−43%) confirmed | 20 wks, active |
| 11-308 | 84 yo Serous Ov Ca | 20 mpk loading | 491 to 1472 (+300%) | SD (+5%) | 22 wks, active |
| 13-311 | 60 yo Serous Ov Ca | 30 mpk loading | 290 to 145 (−31%) | PD (+30%) | 12 wks, (offstudy) |
| 13-312 | 40 yo Serous Ov Ca | 30 mpk loading (reduced to 20) | 65 to 29 (−55%) | SD (−2%) | 11 wks, active |

In particular, 4 of the 5 patients with ovarian/fallopian tube cancer showed a decrease in CA125. See FIG. 1, showing the percent change in baseline CA125(%).

01-312: Weekly dose 20 mg/kg
11-305 and 11-308: Loading dose of 20 mg/kg
13-311 and 13-312: Loading dose of 30 mg/kg 11-305 and 01-312 were also analyzed with scans at baseline and 8 weeks. The scans are shown in FIGS. 2-8. The Figures show that tumor mass decreased substantially from baseline to 8 weeks in each patient. Of note, patients with other solid tumor types, including pancreatic cancer, have been treated at similar doses to-date without achieving an objective response on therapy.

Example 3: Treatment of Ovarian Cancer Sub-Types with Anti-CD47 Antibody

Ovarian cancer patients are selected for administration of anti-CD47 antibody.

Ovarian cancers can include serous tumor, mucinous tumor, clear cell tumor, endometriod tumor, transitional cell tumor, Brenner tumor, carcinosarcoma tumor, mixed epithelial tumor, borderline epithelial tumor, undifferentiated carcinoma tumor, fallopian tube tumor, or primary peritoneal tumor.

A 1 mg/kg priming dose of Hu-5F9-G4 is administered to each patient. 7 days later a therapeutic dose (e.g., 20, 30, 45, 60, or 67.5 mg/kg) of Hu-5F9-G4 is administered. Hu-5F9-G4 is re-administered regularly at a therapeutic dose following the original therapeutic dose, e.g., every 1, 2, 3, or 4 weeks. Each patient is monitored regularly for safety and efficacy.

It is found that Hu-5F9-G4 is efficacious in treating ovarian cancer in human female patients. It is found that CA125 is reduced in certain patients relative to baseline. It is found that tumor mass decreases in certain patients relative to baseline.

Example 4: Treatment of Ovarian Cancer with Anti-CD47 Antibody and an Additional Agent Ovarian cancer patients are selected for administration of anti-CD47 antibody.

Ovarian cancers can include serous tumor, mucinous tumor, clear cell tumor, endometriod tumor, transitional cell tumor, Brenner tumor, carcinosarcoma tumor, mixed epithelial tumor, borderline epithelial tumor, undifferentiated carcinoma tumor, fallopian tube tumor, or primary peritoneal tumor.

A 1 mg/kg priming dose of Hu-5F9-G4 is administered to each patient. 7 days later a therapeutic dose (e.g., 20, 30, 45, 60, or 67.5 mg/kg) of Hu-5F9-G4 is administered. Hu-5F9-G4 is re-administered regularly at a therapeutic dose following the original therapeutic dose, e.g., every 1, 2, 3, or 4 weeks.

Each patient is also administered an additional agent.

The additional agent can be a chemotherapeutic agent, a VEGF inhibitor, a PARP inhibitor, an immune checkpoint inhibitor, an immuno-oncology agent, and/or a folate inhibitor.

A chemotherapeutic agent can be Platinum (cisplatin/carboplatin). A chemotherapeutic agent can be Taxane (paclitaxel (TAXOL®) or docetaxel (TAXOTERE®)), Gemcitabine, Albumin-bound paclitaxel (nab-paclitaxel, ABRAXANE®), Altretamine (HEXALEN®), Capecitabine (XELODA®), Cyclophosphamide (CYTOXAN®), Etoposide (VP-16), Gemcitabine (GEMZAR®), Ifosfamide (IFEX®), Irinotecan (CPT-11, CAMPTOSAR®), Liposomal doxorubicin (DOXIL®), Melphalan, Pemetrexed (ALIMTA®), Topotecan, Vinorelbine (NAVELBINE®), or Trabectedin (YONDELIS®).

A VEGF inhibitor can be bevacizumab (AVASTIN®), regorafenib (STIVARGA®), or aflibercept (EYLEA®).

A PARP inhibitor can be Rucaparib (RUBRACA®), Niraparib (ZEJULA®), Olaparib (LYNPARZA®), Talazoparib (BMN-673), or Veliparib (ABT-888).

An immune checkpoint inhibitor can inhibit at least one of CTLA4, PD1, and PDL1.

A folate inhibitor can inhibit folate metabolism or target folate receptor.

Hu-5F9-G4 and the additional agent can be administered concurrently or sequentially.

Each patient is monitored regularly for safety and efficacy.

It is found that Hu-5F9-G4 in combination with the additional agent is efficacious in treating ovarian cancer in human female patients. It is found that CA125 is reduced in certain patients relative to baseline. It is found that tumor mass decreases in certain patients relative to baseline.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method of treating a human subject having an epithelial ovarian cancer or reducing the size of the epithelial ovarian cancer in the human subject, comprising administering an anti-CD47 antibody to the subject;
   wherein the human subject is platinum resistant, and
   wherein the anti-CD47 antibody is Hu5F9-G4.

2. The method of claim 1, wherein the epithelial ovarian cancer is serous tumor, mucinous tumor, clear cell tumor, endometrioid tumor, transitional cell tumor, Brenner tumor, carcinosarcoma tumor, mixed epithelial tumor, borderline epithelial tumor, undifferentiated carcinoma tumor, fallopian tube tumor, or primary peritoneal tumor.

3. The method of claim 1, wherein the epithelial ovarian cancer is serous tumor, optionally wherein the serous ovarian cancer is low grade or high grade as determined by histological analysis subtyping.

4. The method of claim 1, further comprising administering at least one additional agent to the human subject, wherein the additional agent comprises at least one of a chemotherapeutic agent, a VEGF inhibitor, a PARP inhibitor, an immune checkpoint inhibitor, an immuno-oncology agent, and a folate inhibitor.

5. The method of claim 4, wherein the chemotherapeutic agent is Taxane, Gemcitabine, Albumin-bound paclitaxel, Altretamine, Capecitabine, Cyclophosphamide, Etoposide, Gemcitabine, Ifosfamide, Irinotecan, Liposomal doxorubicin, Melphalan, Pemetrexed, Topotecan, Vinorelbine, or Trabectedin.

6. The method of claim 4, wherein the additional agent is a VEGF inhibitor, optionally bevacizumab, regorafenib, or aflibercept.

7. The method of claim 4, wherein the additional agent is a PARP inhibitor, optionally the PARP inhibitor is Rucaparib, Niraparib, Olaparib, Talazoparib, or Veliparib.

8. The method of claim 4, wherein the additional agent is an immune checkpoint inhibitor, optionally wherein the additional agent inhibits at least one of CTLA4, PD1, and PDL1.

9. The method of claim 4, wherein the additional agent is a folate inhibitor that inhibits folate metabolism or targets the folate receptor.

10. The method of claim 1, wherein the anti-CD47 antibody and an additional agent are administered concurrently or sequentially.

11. The method of claim 1, wherein the antibody is formulated in a pharmaceutical composition with a pharmaceutically acceptable excipient.

12. The method of claim 1, wherein the antibody is administered intravenously, intra-abdominally, or intra-tumorally.

13. The method of claim 1, wherein administration of the antibody reduces the level of at least one of CA125, HE4 (human epididymis protein 4), CA-72-4, CA-19-9 and CEA; compared to baseline.

14. The method of claim 1, wherein the anti-CD47 antibody is administered to the subject as a dose ranging from about 20 to about 67.5 mg/kg of antibody, or as a specific dose of 20 mg/kg of antibody, 30 mg/kg of antibody, 45 mg/kg of antibody, 60 mg/kg of antibody, or 67.5 mg/kg of antibody.

15. The method of claim 1, wherein an infusate is delivered over a period of about 1-3, 8-10, 1, 2, 3, 4, 5, 6, 7, 8, 9, or 10 hour(s).

16. The method of claim 1, wherein a therapeutically effective dose of the anti-CD47 antibody is sufficient to achieve a circulating level of greater than 100, 250, 500, or 1000 μg/ml of the anti-CD47 antibody for a sustained period of time, optionally wherein the sustained period of time is 1-28, 7-28, 7-21, 14-28, or 21-28 days.

17. The method of claim 1, wherein a therapeutically effective dose of the anti-CD47 antibody is administered about every 7, 14, 21, or 28 days.

* * * * *

SEQUENCE LISTING

<160> NUMBER OF SEQ ID NOS: 2

<210> SEQ ID NO 1
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Asn Met His Trp Val Arg Gln Ala Pro Gly Gln Arg Leu Glu Trp Met
        35                  40                  45

Gly Thr Ile Tyr Pro Gly Asn Asp Asp Thr Ser Tyr Asn Gln Lys Phe
    50                  55                  60

Lys Asp Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

```
Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 2
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Gly Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```